United States Patent
Maruyama et al.

(10) Patent No.: US 10,926,907 B2
(45) Date of Patent: Feb. 23, 2021

(54) PTP PACKAGING MACHINE

(71) Applicant: CKD Corporation, Aichi (JP)

(72) Inventors: Shunji Maruyama, Aichi (JP);
Tsuyoshi Ohyama, Aichi (JP);
Norihiko Sakaida, Aichi (JP)

(73) Assignee: CKD CORPORATION, Aichi (JP)

( * ) Notice: Subject to any disclaimer, the term of this patent is extended or adjusted under 35 U.S.C. 154(b) by 200 days.

(21) Appl. No.: 16/025,108

(22) Filed: Jul. 2, 2018

(65) Prior Publication Data

US 2018/0305058 A1    Oct. 25, 2018

Related U.S. Application Data

(63) Continuation of application No. PCT/JP2016/069597, filed on Jul. 1, 2016.

(30) Foreign Application Priority Data

Jan. 26, 2016   (JP) .............................. JP2016-012170

(51) Int. Cl.
| | |
|---|---|
| *B65B 57/14* | (2006.01) |
| *B65B 35/26* | (2006.01) |
| *B65B 35/08* | (2006.01) |
| *B65B 57/16* | (2006.01) |
| *B65B 57/12* | (2006.01) |
| *B65B 57/10* | (2006.01) |
| *A61J 1/03* | (2006.01) |

(Continued)

(52) U.S. Cl.
CPC .............. *B65B 57/14* (2013.01); *A61J 1/035* (2013.01); *B65B 9/045* (2013.01); *B65B 35/08* (2013.01);

(Continued)

(58) Field of Classification Search
CPC ......... B65B 57/14; B65B 9/045; B65B 35/08; B65B 35/26; B65B 57/10; B65B 57/12;

(Continued)

(56) References Cited

U.S. PATENT DOCUMENTS

| | | | | | |
|---|---|---|---|---|---|
| 4,266,477 | A | * | 5/1981 | Ackley | ................... B41F 17/36 |
| | | | | | 101/40 |
| 4,353,456 | A | * | 10/1982 | Yamamoto | .............. A61J 3/074 |
| | | | | | 101/40 |

(Continued)

FOREIGN PATENT DOCUMENTS

| | | |
|---|---|---|
| JP | H05-270507 A | 10/1993 |
| JP | H08-217027 A | 8/1996 |

(Continued)

OTHER PUBLICATIONS

International Search Report for corresponding International Application No. PCT/JP2016/069597, dated Sep. 13, 2016 (5 pages).

*Primary Examiner* — Sameh Tawfik
(74) *Attorney, Agent, or Firm* — Osha Bergman Watanabe & Burton LLP

(57) ABSTRACT

A PTP packaging machine includes: a filler that fills a predetermined content into pocket portions formed in a strip-shaped container film; a sealer that is provided on a downstream side of the filler and mounts a strip-shaped cover film to the container film to close the pocket portions and obtain a strip-shaped PTP film including the cover film mounted to the container film; and a puncher that is provided on a downstream side of the sealer and punches out an expected sheet portion of the PTP film that is a region of eventually forming a predetermined PTP sheet and thereby obtain the PTP sheet.

10 Claims, 14 Drawing Sheets

(51) Int. Cl.
*B65B 9/04* (2006.01)
*B65D 75/36* (2006.01)
*B65B 5/10* (2006.01)
*G16H 20/13* (2018.01)

(52) U.S. Cl.
CPC .............. *B65B 35/26* (2013.01); *B65B 57/10* (2013.01); *B65B 57/12* (2013.01); *B65B 57/16* (2013.01); *B65D 75/367* (2013.01); *A61J 2200/70* (2013.01); *B65B 5/103* (2013.01); *G16H 20/13* (2018.01)

(58) Field of Classification Search
CPC .......... B65B 57/16; B65B 5/103; A61J 1/035; A61J 2200/70; B65D 75/16; G16H 20/13
USPC ............................................................ 53/54
See application file for complete search history.

(56) References Cited

U.S. PATENT DOCUMENTS

| | | | |
|---|---|---|---|
| 5,454,464 A * | 10/1995 | Yamamoto | B65G 47/1485 198/384 |
| 5,802,804 A * | 9/1998 | Esposti | B65B 9/045 53/246 |
| 6,941,729 B2 * | 9/2005 | Dal Pozzo | B29C 66/83413 53/453 |
| 7,407,050 B2 * | 8/2008 | Maruyama | B65B 9/045 198/384 |
| 7,797,909 B2 * | 9/2010 | Ream | A23G 3/0097 53/111 R |
| 9,139,320 B2 * | 9/2015 | Mayer | B65B 57/16 |
| 2010/0033639 A1 * | 2/2010 | Maruyama | H04N 5/44513 348/744 |
| 2010/0303738 A1 | 12/2010 | Ream et al. | |
| 2011/0216290 A1 * | 9/2011 | Maruyama | H04N 9/3185 353/101 |

FOREIGN PATENT DOCUMENTS

| | | |
|---|---|---|
| JP | H10-510785 A | 10/1998 |
| JP | 2004-28604 A | 1/2004 |
| JP | 2004-59036 A | 2/2004 |
| JP | 2004-196422 A | 7/2004 |

* cited by examiner

| SERIAL NUMBER | | | | | | | | | | | | | | | |
|---|---|---|---|---|---|---|---|---|---|---|---|---|---|---|---|
| LA4 | | | | LA3 | | | | LA2 | | | | LA1 | | | |
| RESULTS | | | | RESULTS | | | | RESULTS | | | | RESULTS | | | |
| J6 | × | J1 | ○ | J6 | ○ | J1 | ○ | J6 | ○ | J1 | ○ | J6 | ○ | J1 | ○ |
| J7 | ○ | J2 | ○ | J7 | ○ | J2 | ○ | J7 | ○ | J2 | ○ | J7 | ○ | J2 | ○ |
| J8 | ○ | J3 | ○ | J8 | ○ | J3 | ○ | J8 | ○ | J3 | ○ | J8 | ○ | J3 | ○ |
| J9 | ○ | J4 | ○ | J9 | ○ | J4 | ○ | J9 | ○ | J4 | ○ | J9 | ○ | J4 | ○ |
| J10 | ○ | J5 | ○ | J10 | ○ | J5 | ○ | J10 | ○ | J5 | ○ | J10 | ○ | J5 | ○ |

PTP PACKAGING MACHINE

BACKGROUND

Technical Field

The present disclosure relates to a PTP packaging machine configured to manufacture a PTP sheet.

Description of Related Art

A PTP sheet is comprised of a container film that has pocket portions filled with contents such as tablets, and a cover film that is mounted to the container film such as to seal openings of the pocket portions. In general, the container film is made of, for example, a transparent resin, and the cover film is made of, for example, a metal foil such as aluminum.

A PTP packaging machine used to manufacture a PTP sheet includes, for example, a pocket portion forming unit configured to form concave pocket portions in a conveyed strip-shaped container film, a filling unit configured to fill contents into the pocket portions, a sealing unit configured to mount a cover film to the container film, and a punching unit configured to punch out a strip-shaped PTP film comprised of the container film and the cover film in the unit of PTP sheets.

Additionally, the PTP packaging machine is provided with an inspection unit along a moving path of the contents, such as a conveyance path of the container film. The inspection unit conducts an inspection with regard to filling or non-filling of contents into the pocket portions and with regard to the abnormality of appearance such as cracking or crack of the content.

A conventionally known technique punches out an expected sheet portion (region that forms a PTP sheet after punching out) that is determined as a defective by an inspection unit, in the unit of sheet and subsequently discharges a defective PTP sheet by a predetermined discharge unit (as described in, for example, Patent Literature 1).

Another proposed technique uses an inspection unit that is provided on an upstream side of a sealing unit to determine filling or non-filling of contents into pocket portions. In the case of a defective determination by the inspection unit, filled contents are sucked out and recovered from the pocket portions of an expected sheet portion that is involved in the defective determination, to be reused (as described in, for example, Patent Literature 2).

CITATION LIST

Patent Literature

PTL 1: JP 1108-217027A
PTL 1: JP 1105-270507A

In the former technique, however, non-defective contents are likely to be filled in the PTP sheet discharged as a defective (defective sheet). Disposal of such a defective sheet including non-defective contents wastes the non-defective contents and is likely to increase the production cost. A possible measure of taking out and recovering the non-defective contents from the defective sheet, on the other hand, takes a lot of trouble for recovery and is likely to damage the contents in the course of taking out.

The latter technique, on the other hand, recovers the contents that are once filled. The contents are thus likely to be damaged and broken in the course of filling or in the course of recovery. Additionally, this technique needs to provide a device for recovering the contents separately. This is likely to cause complication and size expansion of the apparatus and increase various costs.

SUMMARY

A PTP packaging machine according to one or more embodiments of the present invention does not waste but uses non-defective contents without any special effort, while more effectively preventing damage of the content, and achieves simplification of the apparatus and reduction of various costs.

Embodiments of the present invention are described. Functions and advantageous effects according to one or more embodiments of the present invention are also described as appropriate.

A PTP packaging machine according to one or more embodiments of the present invention comprises a filling unit configured to fill a predetermined content into pocket portions formed in a strip-shaped container film that is conveyed; a sealing unit provided on a downstream side of the filling unit and configured to mount a strip-shaped cover film to the container film such as to close the pocket portions and thereby obtain a strip-shaped PTP film including the cover film mounted to the container film; and a punching unit provided on a downstream side of the sealing unit and configured to punch out an expected sheet portion of the PTP film that is a region of eventually forming a predetermined PTP sheet and thereby obtain the PTP sheet. The filling unit comprises a rotating drum having a plurality of sucking portions that are formed in an outer circumference of the rotating drum to suck the content, the rotating drum being configured such that the sucking portion moves from a predetermined supply position through a predetermined filling position and returns to the supply position, along with rotation of the rotating drum; a supply unit including a supply changeover unit configured to change over between supply and non-supply of the content to the sucking portion located at the supply position; a sucking state changeover unit configured to individually change over each of the sucking portions to a sucking state or a non-sucking state, the sucking state changeover unit setting the sucking portion in the non-sucking state at the filling position so as to fill the content from the sucking portion into the pocket portion, while keeping the sucking portion in the sucking state at the filling position so as not to fill the content into the pocket portion; an imaging unit configured to take an image of the content that is sucked by the sucking portion or that is to be sucked by the sucking portion at a stage before the sucking portion reaches the filling position; a quality determination unit configured to determine quality of appearance of the content, based on image data obtained by the imaging unit; a sucking state control unit configured to control the sucking state changeover unit, based on a determination result by the quality determination unit; and a supply control unit configured to control the supply changeover unit, based on the determination result by the quality determination unit. When the expected sheet portion including a pocket portion, which the content determined as a defective by the quality determination unit is to be filled in, is identified as a defective sheet portion, the sucking state control unit controls the sucking state changeover unit to maintain the sucking portion corresponding to the content determined as a non-defective product by the quality determination unit, among the contents to be filled into the pocket portions of the defective sheet portion, in the sucking state at least at the filling position. The supply control unit controls the supply changeover unit not to supply the content to the sucking portion corresponding to the content determined as the non-defective product, at the supply position.

In the configuration according to one or more embodiments of the present invention, when the quality determination unit provides a defective determination, a non-defective content is not supplied to the expected sheet portion to which the content involved in this defective determination is to be supplied (defective sheet portion) at the filling position but is kept sucked by the sucking portion. A punched-out defective sheet accordingly does not include any non-defective content. This configuration does not need to take out the non-defective content from the defective sheet with a view to reusing the non-defective content and does not waste the non-defective content even when the defective sheet is disposed directly.

Additionally, in the configuration according to one or more embodiments of the present invention, the sucking portion that sucks and holds a non-defective content is moved again to the supply position and to the filling position along with rotation of the rotating drum. No new content is, however, supplied to this sucking portion at the supply position, and this sucking portion is moved to the filling position while maintaining the suction and retention of the non-defective content. When all the other contents that are to be supplied to the expected sheet portion to which this non-defective content is to be supplied, are non-defective, this non-defective content is filled into the pocket portion at the filling position. Accordingly, a non-defective content involved in a defective sheet portion is neither filled into the pocket portion nor recovered from the pocket portion but is kept in the state of suction and retention at the filling position to be used for subsequent filling.

As described above, the configuration according to one or more embodiments of the present invention does not waste but uses the non-defective content with no special effort, while more effectively preventing damage of the content. This configuration does not require any separate device for recovery of the content and thereby achieves simplification of the apparatus and reduction of various costs.

In the PTP packaging machine according to one or more embodiments of the present invention, the sucking state control unit may control the sucking state changeover unit to set the sucking portion corresponding to the content determined as the defective by the quality determination unit, among the contents to be filled into the pocket portions of the defective sheet portion, in the non-sucking state at least at the filling position.

The configuration according to one or more embodiments of the present invention supplies only the defective content to the defective sheet portion, while not supplying the non-defective content. Accordingly, only a defective content is filled in a defective sheet. This configuration enables the type of abnormality to be readily identified by observation of the filled content. As a result, this configuration readily identifies the inspection item of the abnormality and enables appropriate measures to be taken promptly.

Additionally, the configuration according to one or more embodiments of the present invention does not require any device for separately discharging the defective content. This more effectively achieves simplification of the apparatus and reduction of various costs.

In the PTP packaging machine according to one or more embodiments of the present invention, the supply unit may comprise an upstream side rotating drum having a plurality of upstream side sucking portions that are formed in an outer circumference of the upstream side rotating drum to suck the content. The upstream side rotating drum may be configured to transfer the content sucked by the upstream side sucking portion, to the sucking portion at the supply position. The imaging unit may comprise a first imaging unit configured to take an image of at least an opposite face that is opposite to a sucked face of the content sucked by the sucking portion; and a second imaging unit configured to take an image of at least an opposite face that is opposite to a sucked face of the content sucked by the upstream side sucking portion. The sucked face of the content may be reversed in a process of transferring the content from the upstream side sucking portion to the sucking portion.

The configuration according to one or more embodiments of the present invention takes images of both the surface and the rear face of the content and thereby performs the quality determination of the content with higher accuracy.

In the PTP packaging machine according to one or more embodiments of the present invention, the supply unit may comprise a supply chute configured to supply the content to the upstream side sucking portion located at a predetermined chute corresponding position. The supply changeover unit may be configured to change over between supply and non-supply of the content from the supply chute to the upstream side sucking portion, so as to change over between supply and non-supply of the content to the sucking portion located at the supply position. The first imaging unit may take an image of the content when the sucking portion reaches a predetermined imaging position. A time period required from a time when all the sucking portions corresponding to one expected sheet portion reach the imaging position to a time when at least one of the sucking portions corresponding to the one expected sheet portion reaches the supply position may be set to be longer than a time period required when the upstream side sucking portion moves from the chute corresponding position to reach the supply position.

In the configuration according to one or more embodiments of the present invention, the supply changeover unit is configured to change over between supply and non-supply of the content from the supply chute to the upstream side sucking portion, so as to change over between supply and non-supply of the content to the sucking portion located at the supply position. This readily changes over between supply and non-supply of the content to the sucking portion, while satisfying the configuration according to the above embodiments.

Additionally, the configuration according to one or more embodiments of the present invention enables the retention or the cancellation of the sucking state of a content sucked by a predetermined sucking portion at the filling position to be determined more reliably before a predetermined upstream side sucking portion that is to transfer the content to the predetermined sucking portion reaches the chute corresponding position. This configuration accordingly enables supply or non-supply of the content to the predetermined upstream side sucking portion to be determined more reliably before the predetermined upstream side sucking portion reaches the chute corresponding position. As a result, the supply changeover unit may be configured as described above.

In the PTP packaging machine according to one or more embodiments of the present invention, the first imaging unit and the second imaging unit may be configured to take an image of a side face of the content that is placed between the sucked face by the sucking portion and the sucked face by the upstream side sucking portion.

The configuration according to one or more embodiments of the present invention conducts an inspection with regard to the side face of the content, as well as the surface and the rear face of the content (both the sucked faces) and thereby further enhances the accuracy of the quality determination. There is no need to perform the quality determination of the side face separately. This configuration shortens the time period required for the quality determination and increases the efficiency of inspection.

DETAILED DESCRIPTION OF EMBODIMENTS

The following describes embodiments of the present invention with reference to drawings.

Figure 1:
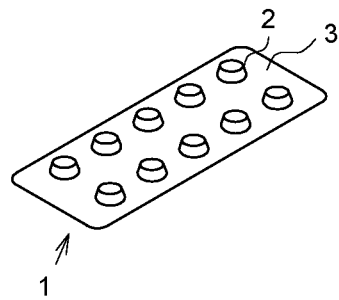
FIG. 1 is a perspective view illustrating a PTP sheet according to one or more embodiments of the present invention.
Figure 2:
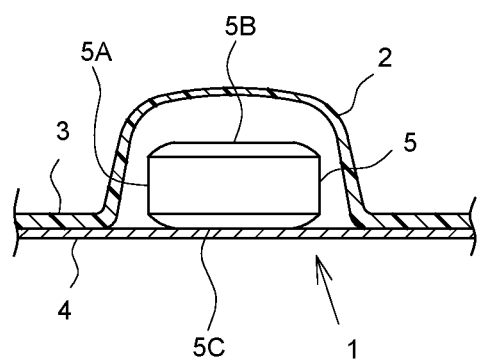
FIG. 2 is a partially enlarged sectional view illustrating the PTP sheet according to one or more embodiments of the present invention.

A PTP sheet 1 is described first. As shown in FIG. 1 and FIG. 2, the PTP sheet 1 includes a container film 3 provided with a plurality of pocket portions 2, and a cover film 4 mounted to the container film 3 such as to close the respective pocket portions 2.

The container film 3 is formed from a transparent or translucent thermoplastic resin material that is relatively hard and has a predetermined rigidity, for example, PP (polypropylene) or PVC (polyvinyl chloride). The cover film 4 is formed from an opaque material (for example, aluminum foil) with a sealant that is made of, for example, a polyester resin and that is applied on a surface thereof.

The PTP sheet 1 is formed in an approximately rectangular shape in planar view and has two arrays of pockets formed along a sheet short direction. Each pocket array is comprised of five pocket portions 2 that are arrayed along a sheet longitudinal direction. Accordingly, a total of ten pocket portion 2 are formed. One tablet 5 is placed as a content in each of the pocket portions 2. According to one or more embodiments of the present invention, the tablet 5 has a disk-shaped body of a circular shape in planar view and is configured to include a side face 5A and a flat surface 5B and a flat rear face 5C arranged to place the side face 5A therebetween.

Figure 3:
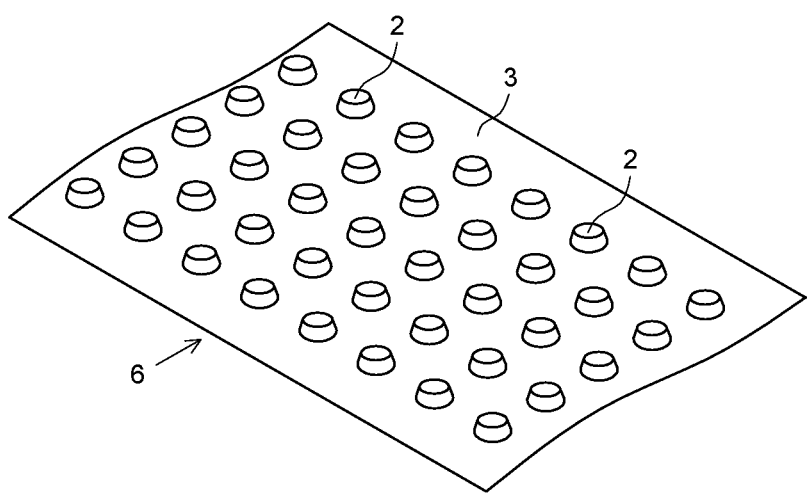
FIG. 3 is a perspective view illustrating a PTP film according to one or more embodiments of the present invention.

The PTP sheet 1 is manufactured by punching sheets from a strip-shaped PTP film 6 (shown in FIG. 3) that is comprised of the strip-shaped container film 3 and the strip-shaped cover film 4.

Figure 4:
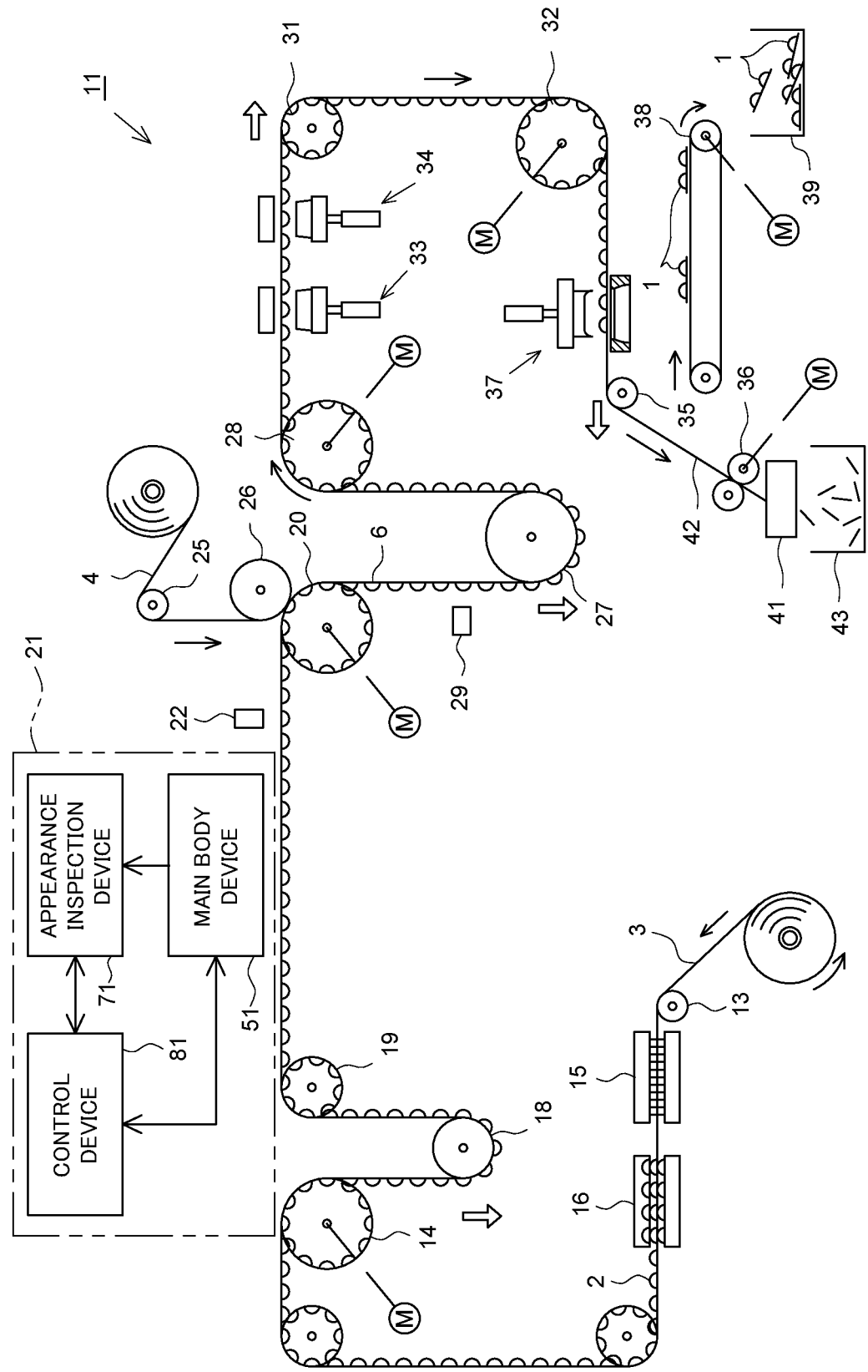
FIG. 4 is a diagram illustrating the schematic configuration of a PTP packaging machine according to one or more embodiments of the present invention.

The following describes the general configuration of a PTP packaging machine 11 used to manufacture the PTP sheet 1 described above, with reference to FIG. 4.

A film roll of the strip-shaped container film 3 is wound in a roll form on a most upstream side of the PTP packaging machine 11. A pullout end of the container film 3 wound in the roll form is guided by a guide roll 13. The container film 3 is then laid on an intermittent feed roll 14 provided on a downstream side of the guide roll 13. The intermittent feed roll 14 is coupled with a motor rotating in an intermittent manner, so as to convey the container film 3 intermittently.

A heating device 15 and a pocket portion forming device 16 are sequentially placed along the conveyance path of the container film 3 between the guide roll 13 and the intermittent feed roll 14. The container film 3 is heated to be relatively soft by the heating device 15, and the plurality of pocket portions 2 are then formed at predetermined positions of the container film 3 by the pocket portion forming device 16. Formation of the pocket portions 2 is executed during an interval between conveying operations of the container film 3 by the intermittent feed roll 14.

The container film 3 fed from the intermittent feed roll 14 is sequentially laid on a tension roll 18, a guide roll 19 and a film receiving roll 20 in this order. The film receiving roll 20 is coupled with a motor rotating at a fixed speed, so as to continuously convey the container film 3 at a fixed speed. The tension roll 18 is configured to pull the container film 3 to the state of tension by an elastic force. This configuration prevents a slack of the container film 3 due to a difference between the conveying operation by the intermittent feed roll 14 and the conveying operation by the film receiving roll 20 and constantly keeps the container film 3 in the state of tension. This configuration accordingly enables the container film 3 to be continuously conveyed without stop between the tension roll 18 and the film receiving roll 20.

A filling device 21 serving as a filling unit (filler) and a pre-sealing inspection device 22 are placed in this order along the conveyance path of the container film 3 between the guide roll 19 and the film receiving roll 20.

The filling device 21 serves to automatically fill the tablets 5 into the pocket portions 2. The configuration of the filling device 21 will be described in detail later.

The pre-sealing inspection device 22 is used to conduct an inspection mainly with regard to any defect of the tablet, for example, to determine whether one tablet 5 is securely filled in each of the pocket portions 2, to identify any abnormality of the tablet 5 and to identify any contamination in the pocket portion 2.

The strip-shaped cover film 4 is also wound on a roll and is placed on a most upstream side.

A pullout end of the cover film 4 wound in the roll form is guided by a guide roll 25 to a heating roll 26. The heating roll 26 is pressed against to be in contact with the film receiving roll 20 described above. The container film 3 and the cover film 4 are fed between the two rolls 20 and 26. The container film 3 and the cover film 4 pass through between the two rolls 20 and 26 in the heated and pressed contact state, so that the cover film 4 is attached to the container film 3 such as to close the respective pocket portions 2. This series of operations provides the PTP film 6 manufactured such that the tablet 5 is filled in each of the pocket portions 2. According to one or more embodiments of the present invention, the film receiving roll 20 and the heating roll 26 constitute a sealing unit (sealer).

The PTP film 6 fed from the film receiving roll 20 is sequentially laid on a tension roll 27 and an intermittent feed roll 28 in this order. The intermittent feed roll 28 is coupled with a motor rotating in an intermittent manner, so as to convey the PTP film 6 intermittently. The tension roll 27 is configured to pull the PTP film 6 to the state of tension by an elastic force. This configuration prevents a slack of the PTP film 6 due to a difference between the conveying operation by the film receiving roll 20 and the conveying operation by the intermittent feed roll 28 and constantly keeps the PTP film 6 in the state of tension.

A post-sealing inspection device 29 is placed along the conveyance path of the PTP film 6 between the film receiving roll 20 and the tension roll 27. This post-sealing inspection device 29 is used to conduct an inspection mainly with regard to a damage such as cracking or breaking of the cover film 4.

The PTP film 6 fed from the intermittent feed roll 28 is sequentially laid on a tension roll 31 and an intermittent feed roll 32 in this order. The intermittent feed roll 32 is coupled with a motor rotating in an intermittent manner, so as to convey the PTP film 6 intermittently. The tension roll 31 is configured to pull the PTP film 6 to the state of tension by an elastic force and serves to prevent a slack of the PTP film 6 between these intermittent feed rolls 28 and 32.

A slit formation device 33 and a stamping device 34 are sequentially placed along the conveyance path of the PTP film 6 between the intermittent feed roll 28 and the tension roll 31. The slit formation device 33 serves to form a cutting slit at predetermined positions of the PTP film 6. The stamping device 34 serves to stamp a mark at predetermined positions of the PTP film 6 (for example, in tag portions).

The PTP film 6 fed from the intermittent feed roll 32 is sequentially laid on a tension roll 35 and a continuous feed roll 36 in this order on a downstream side of the intermittent feed roll 32. A sheet punching device 37 serving as a punching unit (puncher) is placed along the conveyance path of the PTP film 6 between the intermittent feed roll 32 and the tension roll 35. The sheet punching device 37 serves to punch out the outer periphery of each expected sheet portion 7 of the PTP film 6 (shown in FIG. 15) that is a portion of eventually forming the PTP sheet 1.

The PTP sheets 1 punched out by the sheet punching device 37 are conveyed by a discharge conveyor 38 and are once accumulated in a finished product hopper 39. The PTP sheet 1 determined as a defective by either of the above inspection devices 22 and 29 (defective sheet) is discharged separately by a non-illustrated defective sheet discharge mechanism.

A cutting device 41 is placed on a downstream side of the continuous feed roll 36. An unrequired film portion 42 that is a residual part (scrap part) remaining in a belt-like form after punching by the sheet punching device 37 is guided by the tension roll 35 and the continuous feed roll 36 and is subsequently led to the cutting device 41. A driven roll is pressed against to be in contact with the continuous feed roll 36, so that the unrequired film portion 42 is placed and conveyed between the driven roll and the continuous feed roll 36. The cutting device 41 serves to cut the unrequired film portion 42 into predetermined dimensions as scraps. These scraps are accumulated in a scrap hopper 43 and are disposed separately.

Each of the rolls, for example, the rolls 14, 19, 20, 28, 31 and 32 described above is arranged such that the roll surface is opposed to the pocket portions 2. The surface of each roll, for example, the roll 14, has recesses that are formed to place the pocket portions 2 therein. This configuration basically suppresses the pocket portions 2 from being crushed. The feeding operation with the pocket portions 2 placed in the recesses of each roll, for example, the roll 14, achieves the smooth intermittent feed and continuous feed.

The following describes the configuration of the filling device 21. The filling device 21 includes a main body device 51, an appearance inspection device 71 and a control device 81.

Figure 5:
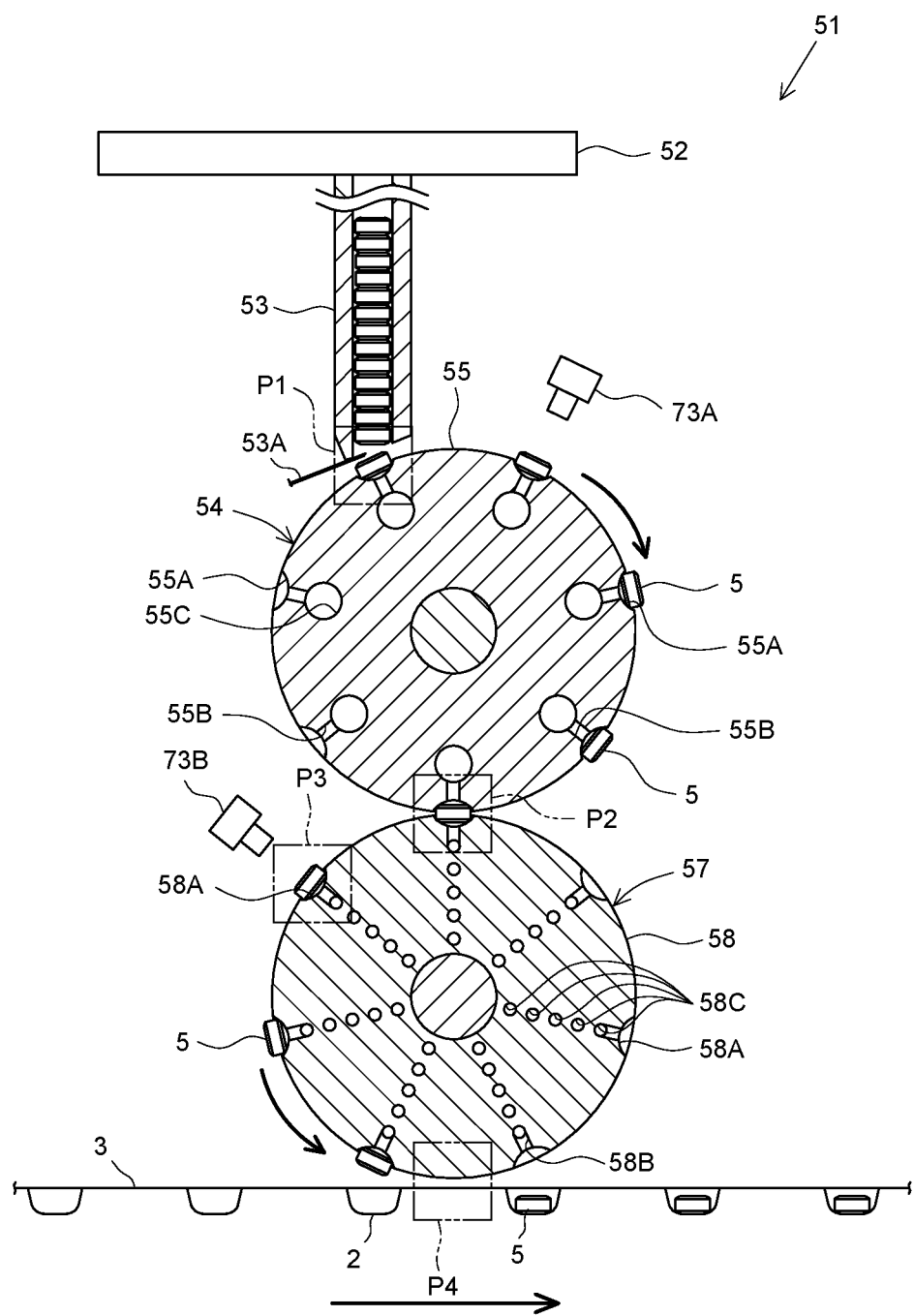
FIG. 5 is a diagram illustrating the schematic configuration of a main body device according to one or more embodiments of the present invention.

The configuration of the main body device 51 is described first. As shown in FIG. 5, the main body device 51 includes a storage unit 52, supply chutes 53, an upstream side drum 54 and a downstream side drum 57, which are provided in this sequence from the upstream side to the downstream side.

The storage unit 52 serves to accumulate the tablets 5. The tablets 5 are sequentially fed from the storage unit 52 to the supply chutes 53.

The supply chutes 53 are in a tubular form, and a plurality of (five according to one or more embodiments) supply chutes 53 are arrayed along axis directions of the above two drums 54 and 57 (depth direction of the sheet surface of FIG. 5). A lower opening of each supply chute 53 is located immediately above the upstream side drum 54, and a shutter 53A is provided near to the lower opening to open and close the lower opening. The opening and closing operations of this shutter 53A are controlled by the control device 81. When the shutter 53A is opened, the tablet 5 drops from the supply chute 53 to be fed toward the upstream side drum 54. According to one or more embodiments of the present invention, the shutters 53A correspond to a supply changeover unit.

Figure 6:
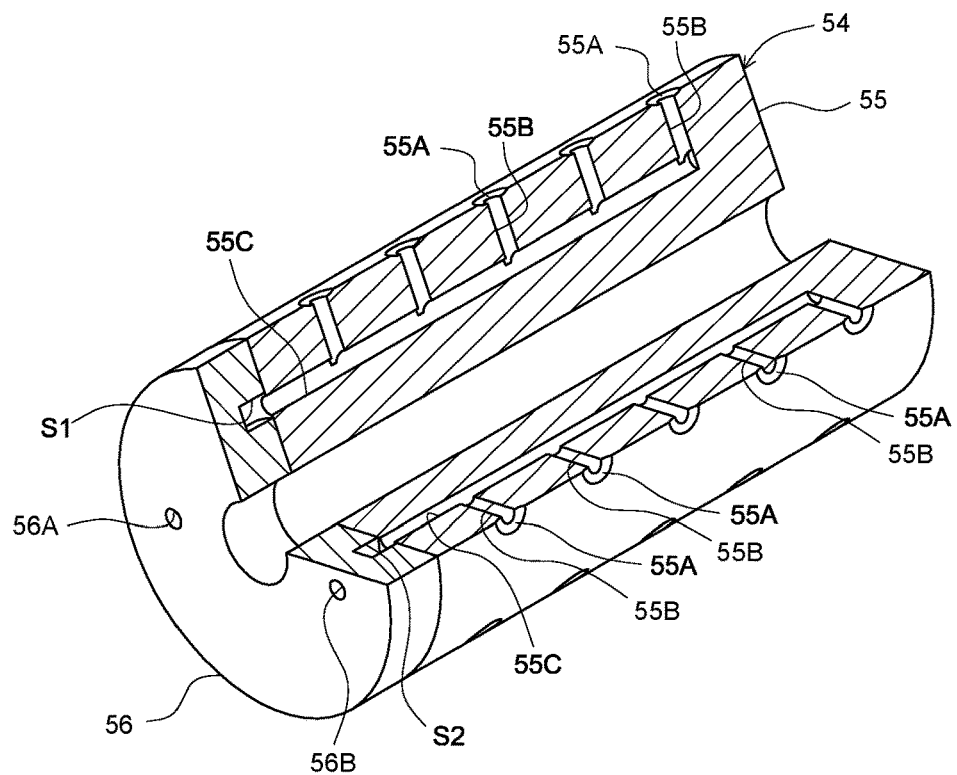
FIG. 6 is a partly broken perspective view illustrating an upstream side drum according to one or more embodiments of the present invention.
Figure 7:
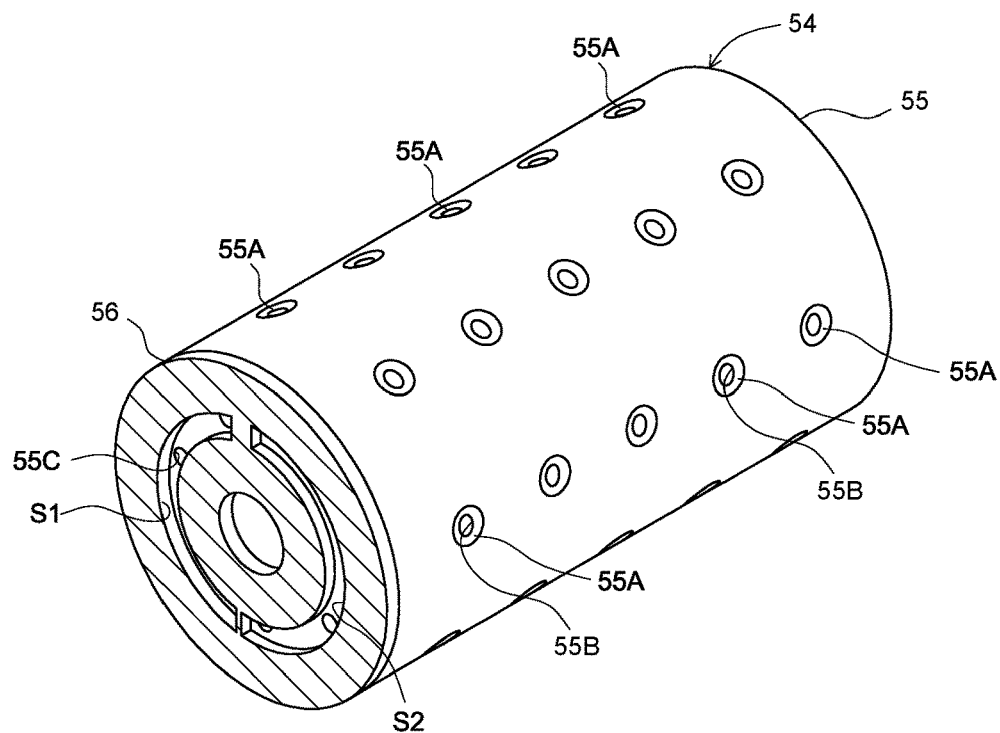
FIG. 7 is a partly broken perspective view illustrating the upstream side drum according to one or more embodiments of the present invention.

As shown in FIG. 6 and FIG. 7, the upstream side drum 54 includes an upstream side rotating drum 55 in a cylindrical shape and an upstream side fixed valve 56 in a disk shape arranged coaxially with the upstream side rotating drum 55.

The upstream side rotating drum 55 is continuously rotated by a non-illustrated drive unit in synchronism with the speed of a downstream side rotating drum 58 described later. The upstream side rotating drum 55 includes a plurality of upstream side sucking portions 55A and a plurality of upstream side air holes 55C.

Figure 8:
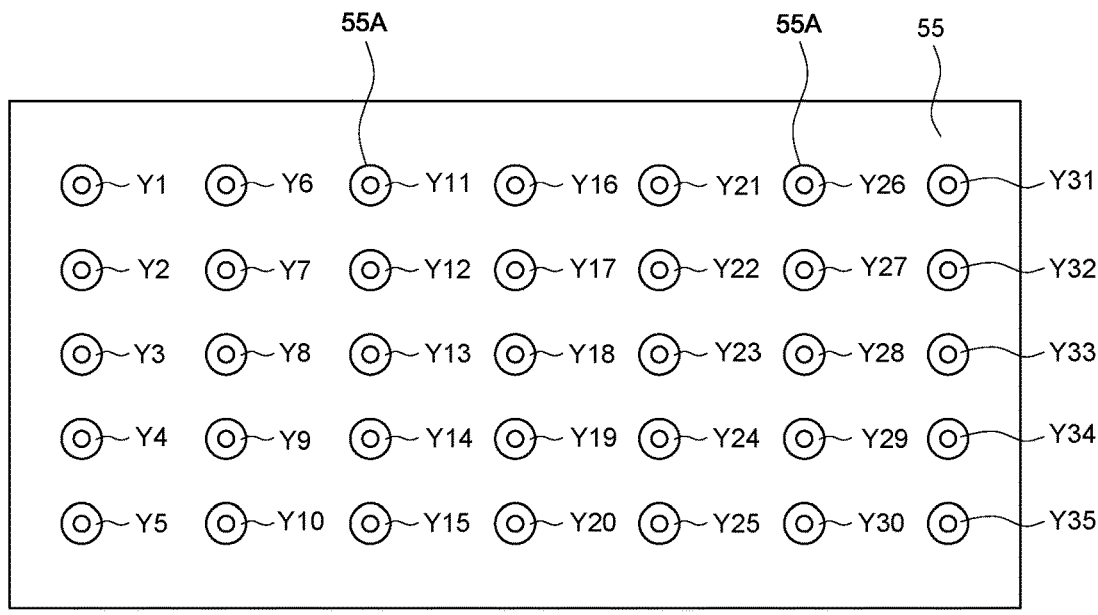
FIG. 8 is a development diagram illustrating an outer circumferential face of an upstream side rotating drum according to one or more embodiments of the present invention.

The upstream side sucking portion 55A includes a recessed part provided in an outer circumferential face of the upstream side rotating drum 55 and an upstream side vacuum port 55B formed to be open at the center of the recessed part. The upstream side sucking portion 55A serves to suck and hold the tablet 5 fed from the supply chute 53 when negative pressure is applied to the upstream side vacuum port 55B. According to one or more embodiments of the present invention, the number of the upstream side sucking portions 55A provided along the axis direction of the upstream side rotating drum 55 is equal to the number of the pocket portions 2 (five according to one or more embodiments) along a width direction of the container film 3, and a plurality of (seven according to one or more embodiments) the upstream side sucking portions 55A are provided at equal intervals along a circumferential direction of the upstream side rotating drum 55. In the description below, the respective upstream side sucking portions 55A may be individually shown by reference signs Y1 to Y35 (as shown in FIG. 8).

Additionally, the upstream side sucking portion 55A is sequentially moved relative to a chute corresponding position P1 and a supply position P2, along with rotation of the upstream side rotating drum 55 (as shown in FIG. 5).

The chute corresponding position P1 denotes a position corresponding to a drop position of the tablet 5 from the supply chute 53. The tablet 5 is fed from the supply chute 53 to the upstream side sucking portion 55A placed at this position.

The supply position P2 denotes a position located vertically below the axis of the upstream side rotating drum 55. At this position, the tablet 5 is transferred from the upstream side sucking portion 55A to a downstream side sucking portion 58A described later.

The upstream side air holes 55C are provided inside of the upstream side rotating drum 55 to be extended in the axis direction of the upstream side rotating drum 55 and to be open to one end face (upstream side fixed valve 56-*side* face) of the upstream side rotating drum 55. A plurality of (seven according to one or more embodiments) the upstream side air holes 55C are provided at equal intervals along the rotating direction of the upstream side rotating drum 55. A plurality of the upstream side vacuum ports 55B arrayed in the axis direction of the upstream side rotating drum 55 are arranged to respectively communicate with one upstream side air hole 55C.

The upstream side rotating drum 55 is provided with a non-illustrated encoder. A signal regarding the rotation angle of the upstream side rotating drum 55 is output at predetermined time intervals from the encoder to the control device 81 and the appearance inspection device 71.

The upstream side fixed valve 56 is provided to cover one end face of the upstream side rotating drum 55 and is configured to be unmovable unlike the upstream side rotating drum 55. The upstream side fixed valve 56 has an upstream side negative pressure space S1 and an air open space S2 that are open to the one end face side of the upstream side rotating drum 55. The spaces S1 and S2 are respectively formed in curved shapes about an axis of the upstream side fixed valve 56.

Figure 12:
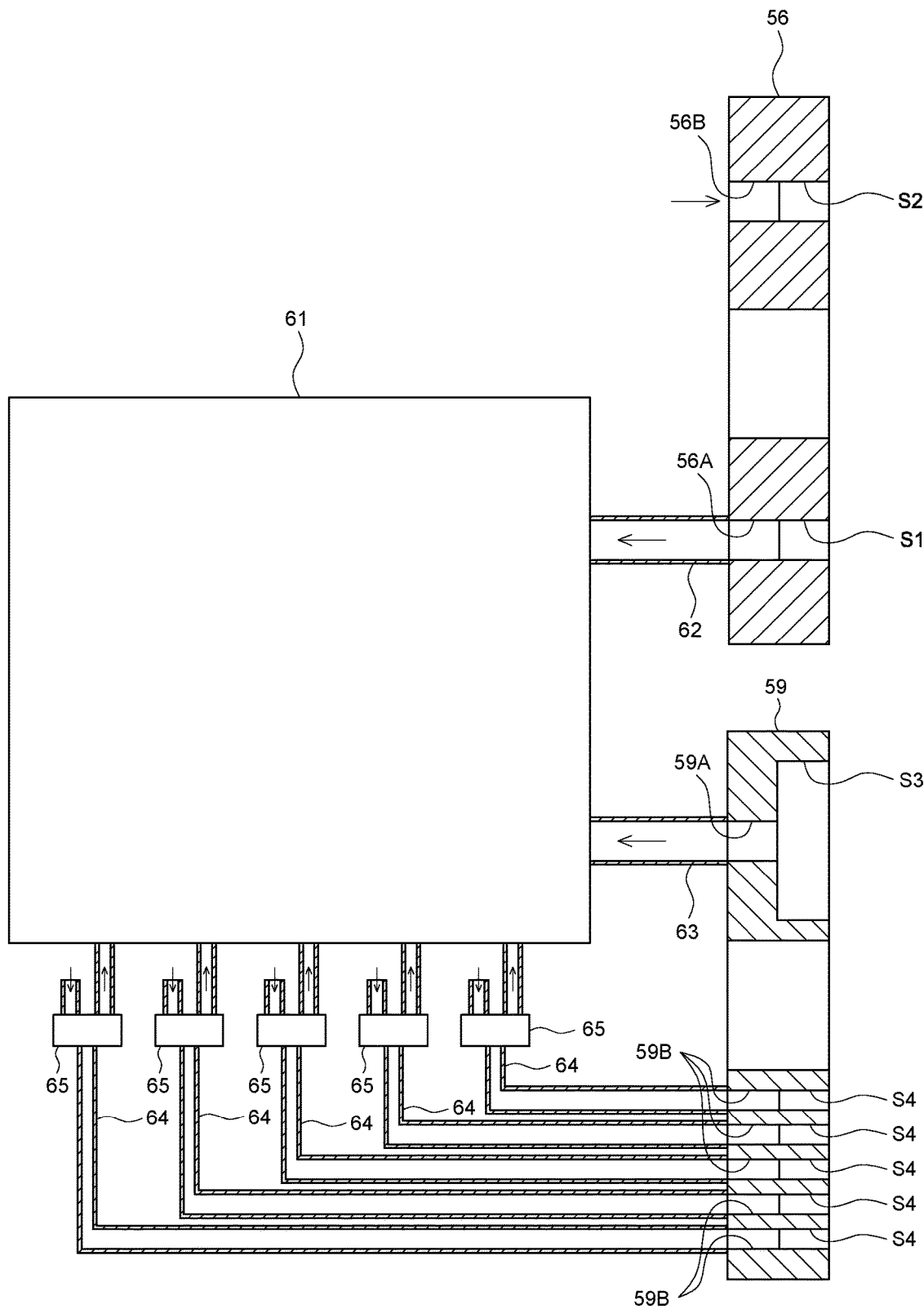
FIG. 12 is a diagram illustrating the connections of respective spaces with a vacuum pump and the like according to one or more embodiments of the present invention.

The upstream side negative pressure space S1 denotes a space that communicates with the upstream side air hole 55C corresponding to the upstream side vacuum port 55B of the upstream side sucking portion 55A when the upstream side sucking portion 55A is located in a region from the chute corresponding position P1 to a position just before the supply position P2. Negative pressure is constantly applied to the upstream side negative pressure space S1 by a predetermined vacuum pump 61 via a through-hole 56A formed in the upstream side fixed valve 56 and a predetermined vent pipe 62 communicating with the through-hole 56A (i.e., The upstream side negative pressure space S1 is constantly vacuumed) (as shown in FIG. 12).

The air open space S2 denotes a space that communicates with the upstream side air hole 55C corresponding to the upstream side vacuum port 55B of the upstream side sucking portion 55A when the upstream side sucking portion 55A is located in a region from the supply position P2 to a position just before the chute corresponding position P1. The air open space S2 is constantly open to the atmosphere via a through-hole 56B formed in the upstream side fixed valve 56 (as shown in FIG. 12).

The above configuration of the upstream side drum 54 causes the upstream side sucking portion 55A located at the chute corresponding position P1 to be ready for suction and to suck and hold the tablet 5 dropping from the supply chute 53. When the upstream side sucking portion 55A sucking and holding the tablet 5 reaches the supply position P2 along with rotation of the upstream side rotating drum 55, the suction and retention of the tablet 5 by the upstream side sucking portion 55A is cancelled, and the tablet 5 is transferred to the downstream side sucking portion 58A. According to one or more embodiments of the present invention, the upstream side drum 54 and the supply chutes 53 correspond to a supply unit (supplier).

Figure 9:
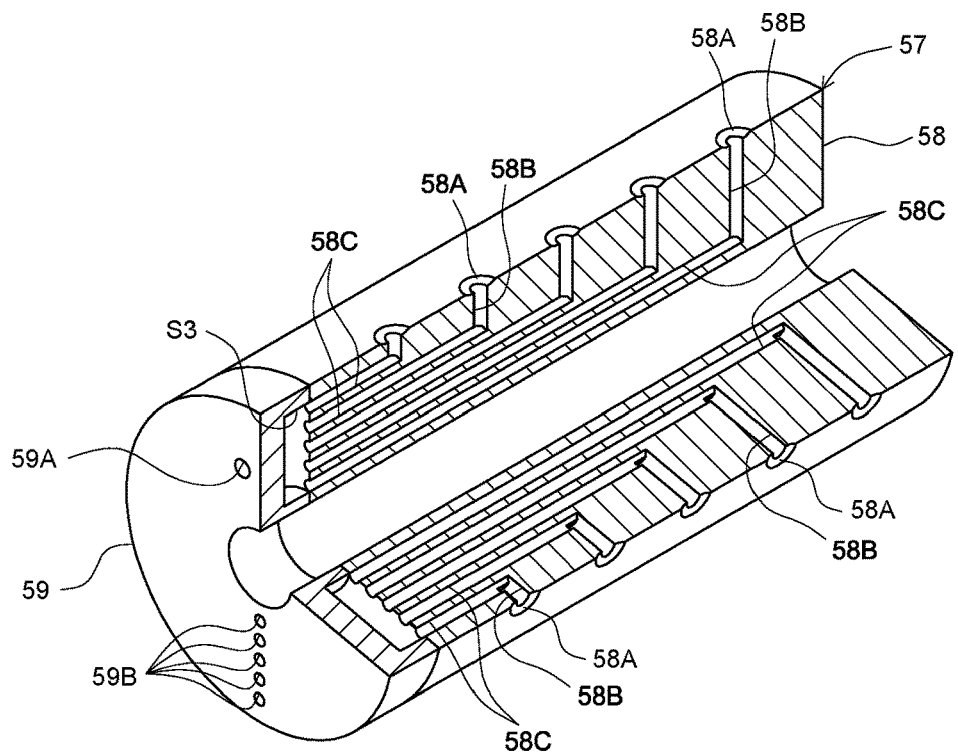
FIG. 9 is a partly broken perspective view illustrating a downstream side drum according to one or more embodiments of the present invention.
Figure 10:
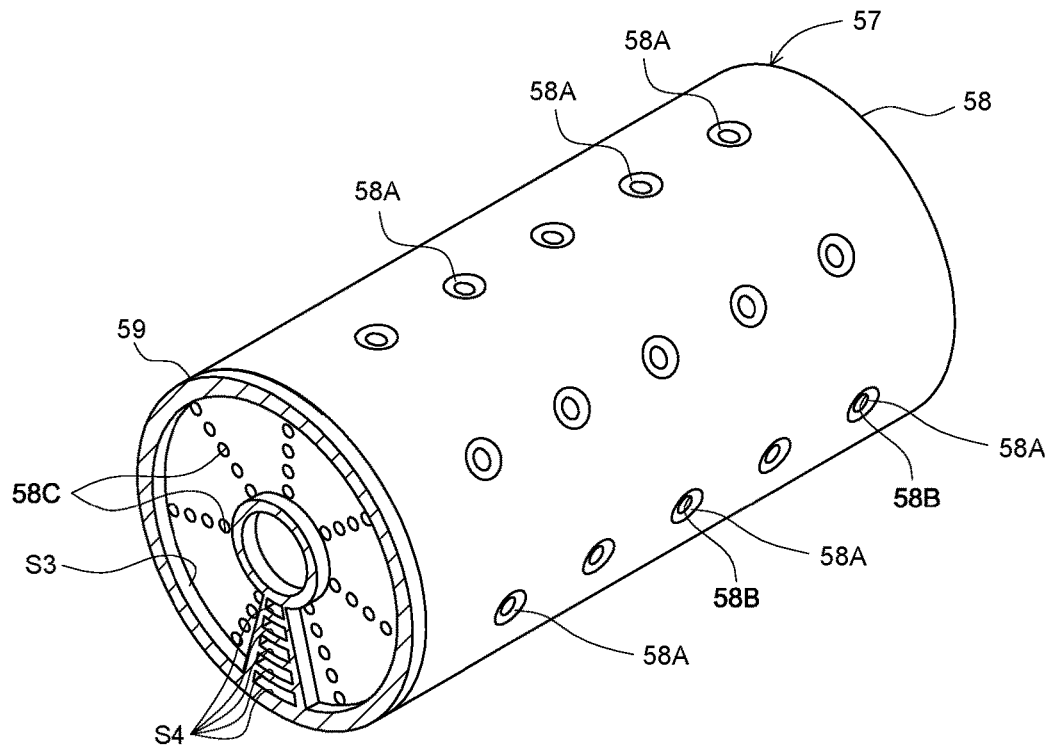
FIG. 10 is a partly broken perspective view illustrating the downstream side drum according to one or more embodiments of the present invention.

As shown in FIG. 9 and FIG. 10, the downstream side drum 57 includes a downstream side rotating drum 58 in a cylindrical shape and a downstream side fixed valve 59 in a disk shape arranged coaxially with the downstream side rotating drum 58. According to one or more embodiments of the present invention, the downstream side rotating drum 58 corresponds to the rotating drum.

The downstream side rotating drum 58 is continuously rotated by a non-illustrated drive unit in synchronism with the speed of the conveyed container film 3. According to one or more embodiments of the present invention, the downstream side rotating drum 58 has an identical diameter with that of the upstream side rotating drum 55 and is rotated at an identical rotation speed with that of the upstream side rotating drum 55. The downstream side rotating drum 58 includes a plurality of downstream side sucking portions 58A and a plurality of downstream side air holes 58C.

Figure 11:
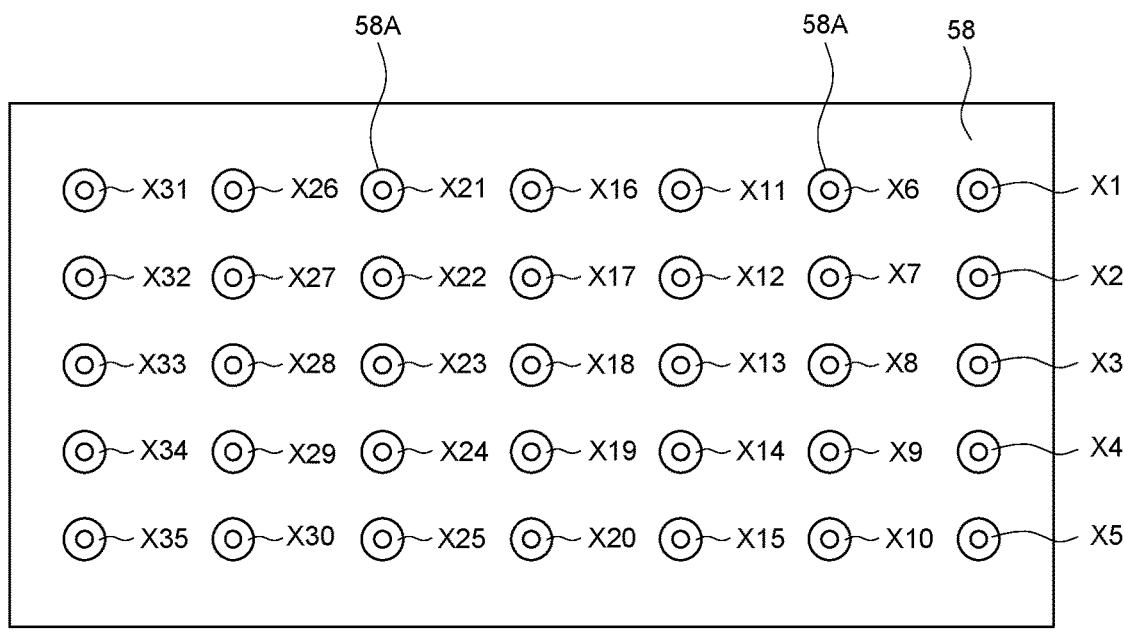
FIG. 11 is a development diagram illustrating an outer circumferential face of a downstream side rotating drum according to one or more embodiments of the present invention.

The downstream side sucking portion 58A includes a recessed part provided in an outer circumferential face of the downstream side rotating drum 58 and a downstream side vacuum port 58B formed to be open at the center of the recessed part. The downstream side sucking portion 58A serves to suck and hold the tablet 5 transferred from the upstream side sucking portion 55A when negative pressure is applied to the downstream side vacuum port 58B. The number of the downstream side sucking portions 58A provided is equal to the number of the upstream side sucking portions 55A. The positions of the downstream side sucking portions 58A arranged in the outer circumferential face of the downstream side rotating drum 58 are respectively aligned with the positions of the corresponding upstream side sucking portions 55A arranged in the outer circumferential face of the upstream side rotating drum 55. In the description below, the respective downstream side sucking portions 58A may be individually shown by reference signs X1 to X35 (as shown in FIG. 11).

According to one or more embodiments of the present invention, the tablet 5 is transferred between the respective sucking portions 55A and 58A having the same numerical value of the reference signs X1 to X35 and Y1 to Y35. For example, the tablet 5 is transferred from the upstream side sucking portion 55A shown by the reference sign Y1 to the downstream side sucking portion 58A shown by the reference sign X1.

Additionally, the downstream side sucking portion 58A is sequentially moved relative to the above supply position P2, an imaging position P3 and a filling position P4, along with rotation of the downstream side rotating drum 58 (as shown in FIG. 5).

The imaging position P3 denotes a position corresponding to a downstream side camera 73B described later. When the downstream side sucking portion 58A is located at this position, an image of the tablet 5 sucked by the downstream side sucking portion 58A is taken by the downstream side camera 73B.

The filling position P4 denotes a position located vertically below the axis of the downstream side rotating drum 58. At this position, the tablet 5 sucked and held by the downstream side sucking portion 58A is filled into the pocket portion 2.

According to one or more embodiments of the present invention, two arrays of the downstream side sucking portions 58A arrayed along the rotating direction of the downstream side rotating drum 58 are used to fill the tablets 5 into the pocket portions 2 of one expected sheet portion 7. According to one or more embodiments of the present invention, a moving distance of the downstream side sucking portion 58A from the state that one array of the downstream side sucking portions 58A arranged on a back side in the rotating direction out of the two arrays of the downstream side sucking portions 58A is located at the imaging position P3 to the state that one array of the downstream side sucking portions 58A arranged on a front side in the rotating direction out of the two arrays of the downstream side sucking portions 58A reaches the supply position P2 is larger than a moving distance of the upstream side sucking portion 55A that is moved from the chute corresponding position P1 to reach the supply position P2. As a result, a time period required from the time when all the downstream side sucking portions 58A corresponding to one expected sheet portion 7 reach the imaging position P3 to the time when at least one of these downstream side sucking portions 58A reaches the supply position P2 is longer than a time period required when the upstream side sucking portion 55A is moved from the chute corresponding position P1 to reach the supply position P2.

The downstream side air holes 58C are provided inside of the downstream side rotating drum 58 to be extended in the axis direction of the downstream side rotating drum 58 and to be open to one end face (downstream side fixed valve 59-*side* face) of the downstream side rotating drum 58. A plurality of (five according to one or more embodiments) the downstream side air holes 58C are arrayed along the radial direction of the downstream side rotating drum 58. A plurality of (seven according to one or more embodiments) the arrays of the downstream side air holes 58C arrayed in the radial direction are provided at equal intervals along the rotating direction of the downstream side rotating drum 58. Each of the downstream side air holes 58C is arranged to communicate with one downstream side vacuum port 58B. One array of the downstream side vacuum ports 58B arrayed in the axis direction of the downstream side rotating drum 58 is arranged corresponding to one array of the downstream side air holes 58C arrayed in the radial direction.

The downstream side rotating drum 58 is provided with a non-illustrated encoder. A signal regarding the rotation angle of the downstream side rotating drum 58 is output at predetermined time intervals from the encoder to the control device 81 and the appearance inspection device 71.

The downstream side fixed valve 59 is provided to cover one end face of the downstream side rotating drum 58 and is configured to be unmovable unlike the downstream side rotating drum 58. The downstream side fixed valve 59 has a downstream side negative pressure space S3 and changeover spaces S4 that are open to one end face side of the downstream side rotating drum 58. The spaces S3 and S4 are respectively formed in curved shapes about an axis of the downstream side fixed valve 59.

The downstream side negative pressure space S3 denotes a space that communicates with the downstream side air hole 58C corresponding to the downstream side vacuum port 58B of the downstream side sucking portion 58A when the downstream side sucking portion 58A is located in a region including the supply position P2 from a position slightly after the filling position P4 to a position just before the filling position P4. Negative pressure is constantly applied to the downstream side negative pressure space S3 by the vacuum pump 61 via a through-hole 59A formed in the downstream side fixed valve 59 and a predetermined vent pipe 63 communicating with the through-hole 59A (i.e., The downstream side negative pressure space S3 is constantly vacuumed) (as shown in FIG. 12). The downstream side negative pressure space S3 has a relatively large width along the radial direction of the downstream side fixed valve 59. Accordingly, the downstream side negative pressure space S3 is arranged to simultaneously communicate with the respective downstream side air holes 58C arrayed along the radial direction.

The changeover space S4 denotes a space that communicates with the downstream side air hole 58C corresponding to the downstream side vacuum port 58B of the downstream side sucking portion 58A when the downstream side sucking portion 58A is located in a region including the filling position P4 from a position just before the filling position P4 to a position slightly after the filling position P4.

A plurality of the changeover spaces S4 are provided at equal intervals along the radial direction of the downstream side fixed valve 59 and are respectively formed in arc shapes. Each of the changeover spaces S4 is arranged to individually communicate with one of the respective downstream side air hole 58C arrayed along the radial direction, along with rotation of the downstream side rotating drum 58. The length of the changeover space S4 along the circumferential direction of the downstream side fixed valve 59 is shorter than the interval of the downstream side air holes 58C along the rotating direction of the downstream side rotating drum 58. This configuration prevents two or more downstream side air holes 58C from simultaneously communicating with one changeover space S4.

Each of the changeover spaces S4 is connected with the vacuum pump 61 via a through-hole 59B formed in the downstream side fixed valve 59 and a predetermined vent pipe 64 communicating with the through-hole 59B. An electromagnetic changeover valve 65 serving as a sucking state changeover unit is provided in the vent pipe 64. The electromagnetic changeover valve 65 serves to change over between the state that negative pressure is applied to the changeover space S4 by the vacuum pump 61 and the state that the changeover space S4 is open to the atmosphere. Changing over the state of the changeover space S4 individually changes over between retention and cancellation of the sucking state in each downstream side sucking portion 58A located at the filling position P4. The electromagnetic changeover valves 65 are electrically connected with the control device 81. The operations of the electromagnetic changeover valves 65 are controlled by the control device 81.

The above configuration of the downstream side drum 57 causes the downstream side sucking portion 58A located at the supply position P2 to be ready for suction and to suck and hold the tablet 5 transferred from the upstream side sucking portion 55A. In this state, a sucked face of the tablet 5 is reversed. For example, when a surface 5B of the tablet 5 is sucked by the upstream side sucking portion 55A, a rear face 5C of the tablet 5 is sucked by the downstream side sucking portion 58A. When the downstream side sucking portion 58A sucking and holding the tablet 5 reaches the filling position P4 along with rotation of the downstream side rotating drum 58, in the state that the corresponding changeover space S4 is open to the atmosphere, the suction of the tablet 5 by the downstream side sucking portion 58A is cancelled, so that the tablet 5 is filled into the pocket portion 2. In the state that negative pressure is applied to the corresponding changeover space S4, on the other hand, the suction of the tablet 5 by the downstream side sucking portion 58A is maintained, so that the tablet 5 is not filled into the pocket portion 2. The downstream side sucking portion 58A maintaining the suction of the tablet 5 is returned to the supply position P2, while keeping the suction state.

Figure 13:
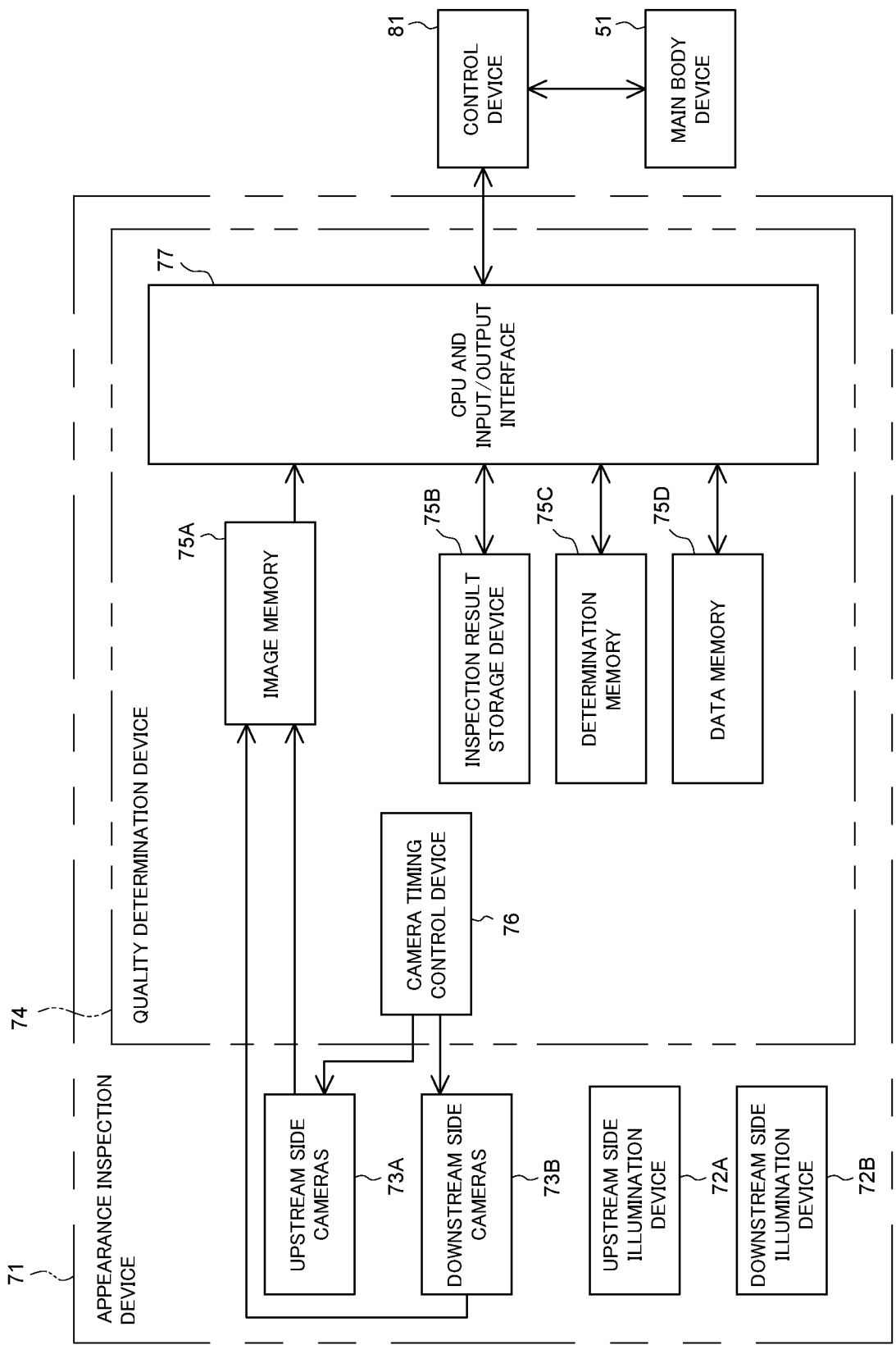
FIG. 13 is a block diagram illustrating the electrical configuration of an inspection device according to one or more embodiments of the present invention.

The following describes the appearance inspection device 71. As shown in FIG. 13, the appearance inspection device 71 includes an upstream side illumination device 72A, a downstream side illumination device 72B, upstream side cameras 73A serving as a second imaging unit (second imager), downstream side cameras 73B serving as a first imaging unit (first imager), and a quality determination device 74 serving as a quality determination unit. According to one or more embodiments of the present invention, both the cameras 73A and 73B correspond to the imaging unit.

The upstream side illumination device 72A is provided corresponding to the upstream side drum 54 to irradiate the tablet 5 placed at a predetermined position between the chute corresponding position P1 and the supply position P2 with predetermined light (for example, near infrared light or visible light).

The downstream side illumination device 72B is provided corresponding to the downstream side drum 57 to irradiate the downstream side sucking portion 58A placed at the imaging position P3 with predetermined light (for example, near infrared light or visible light), so as to illuminate the tablet 5 sucked by the downstream side sucking portion 58A.

The upstream side camera 73A and the downstream side camera 73B respectively take images of the tablets 5 irradiated with light by the illumination devices 72A and 72B. According to one or more embodiments of the present invention, a CCD camera that includes a convex lens and has sensitivity in a wavelength domain of the light emitted from the illumination device 72A or 72B is employed for the cameras 73A and the cameras 73B. This is, however, not essential, but a CMOS camera may be employed.

A plurality of the cameras 73A and a plurality of the cameras 73B are provided corresponding to the number of the sucking portions 55A along the axis direction of the rotating drum 55 and the number of the sucking portions 58A along the axis direction of the rotating drum 58. Each of the cameras 73A and 73B is configured to take an image of one tablet 5. According to a modification, a relatively small number of cameras 73A and 73B (for example, one each) may be provided to simultaneously take images of a plurality of tablets 5 by using predetermined mirrors.

The upstream side camera 73A is provided corresponding to the upstream side drum 54 and is arranged to take an image of the tablet 5 conveyed by the upstream side rotating drum 55. According to one or more embodiments of the present invention, the upstream side camera 73A is configured such that the distance from the convex lens to its focal point (focal length) is larger than the distance from the convex lens to the tablet 5 as an imaging object. Accordingly, this configuration enables an image of the side face 5A as well as the face of the tablet 5 opposite to the sucked face (i.e., one of the surface 5B and the rear face 5C) to be taken by the upstream side camera 73A.

The downstream side camera 73B is provided corresponding to the downstream side drum 57 and is arranged to take an image of the tablet 5 conveyed to the imaging position P3 by the downstream side rotating drum 58. According to one or more embodiments of the present invention, like the upstream side camera 73A, the downstream side camera 73B is configured such that the focal length is larger than the distance from the convex lens to the tablet 5 as the imaging object. Accordingly, this configuration enables an image of the side face 5A as well as the face of the tablet 5 opposite to the sucked face (i.e., the other of the surface 5B and the rear face 5C) to be taken by the downstream side camera 73B. The configuration according to one or more embodiments of the present invention thus enables an image of the entire outer surface of the tablet 5 to be taken by both the cameras 73A and 73B.

Image data (luminance image data or color image data) taken by the cameras 73A and 73B are converted into digital signals inside of the cameras 73A and 73B and are then input in the form of digital signals into the quality determination device 74.

The quality determination device 74 is configured as a computer system including, for example, a CPU as an arithmetic unit, a ROM provided to store various programs and a RAM provided to temporarily store various data such as calculation data and input/output data and is capable of executing various processes such as image processing.

The quality determination device 74 includes an image memory 75A, an inspection result storage device 75B, a determination memory 75C, a data memory 75D, a camera timing control device 76, and a CPU and input/output interface 77 and is configured to execute, for example, various image processing techniques such as binarization process and lump processing and a quality determination process (inspection process).

The image memory 75A stores two-dimensional image data (image data) of taken images output from the cameras 73A and 73B. An inspection is conducted, based on the image data stored in this image memory 75A. Image data may be processed in the course of the inspection. An available data processing technique may be, for example, masking process or shading correction. There are technical limitations in uniformly irradiating an entire imaging region of the tablet 5 with the light of the illumination devices 72A and 72B. The shading correction accordingly corrects a variation in luminosity of the light due to the difference in position. Binarized image data obtained by the binarization process of the image data and masking image data obtained by the masking process in the course of inspection are also stored into this image memory 75A.

Figures 14, 15:
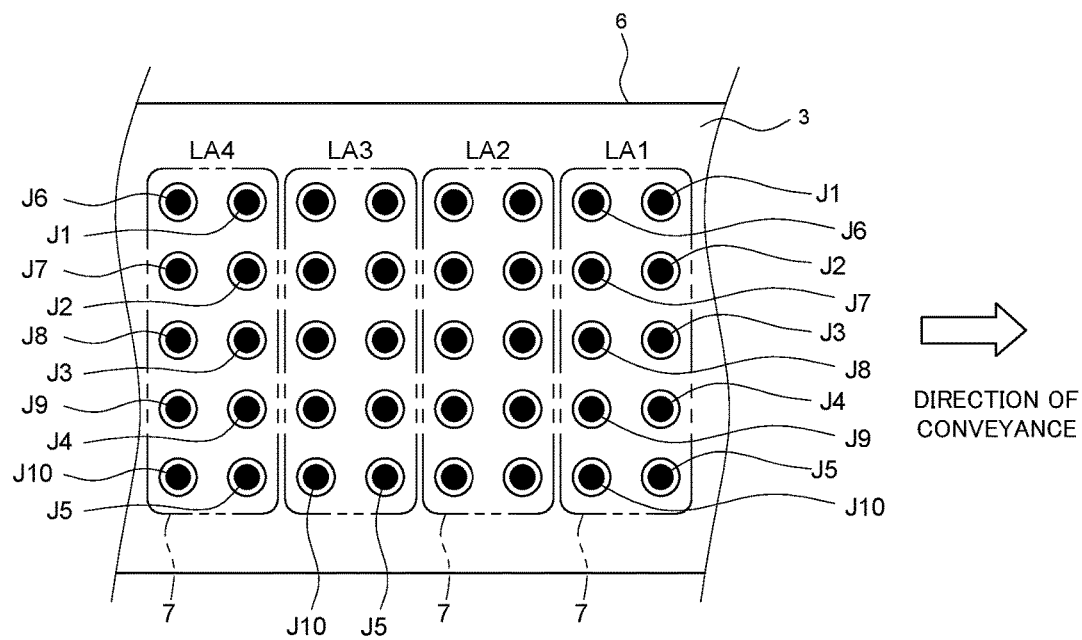
FIG. 14 is a diagram illustrating one example of quality determination results according to one or more embodiments of the present invention.
FIG. 15 is a diagram illustrating serial number and tablet numbers in expected sheet portions according to one or more embodiments of the present invention.

The inspection result storage device 75B stores data such as coordinates with regard to the image data, data on quality determination results of inspection objects and statistic data obtained by stochastically processing this data. The inspection result storage device 75B stores information indicating the quality determination results of the respective tablets 5 indicated by predetermined tablet numbers J1 to J10 (shown in FIG. 15), in combination with serial numbers LA1, LA2, LA3, LA4, . . . (shown in FIG. 15) used to identify expected sheet portions 7 to which the respective tablets 5 are to be supplied (as shown in FIG. 14; non-defective products are shown by the "open circle" and defectives are shown by the "cross mark" in FIG. 14).

The quality determination of the tablet 5 is executed with regard to a plurality of inspection items. The tablet 5 is identified as a non-defective product when all the inspection items provide good results. The tablet 5 is identified as a defective when at least one inspection item provides a poor result. The inspection items include, for example, an item regarding whether the tablet 5 has any cracking (item regarding "tablet cracking"), an item regarding whether the tablet 5 has any crack (item regarding "tablet crack"), an item regarding whether the surface layer of the tablet 5 has any peeling (item regarding "tablet surface peeling") and an item regarding whether the shape and the size of the tablet 5 meet the requirements of a manufacturing item (item regarding "tablet shape/size difference").

The determination memory 75C stores reference values used for the inspection (for example, threshold values). The reference value is set for each inspection item. The reference values used for the inspection include, for example, the dimensions of the tablet 5 or the like, the shapes and dimensions of various window frames used to specify various inspection regions, threshold values involved in binarization process, reference values involved in area determination and color reference values involved in color identification test.

The data memory 75D is configured by, for example, a hard disk drive and stores the date and the time of defective determination and inspection conditions employed for the inspection.

The camera timing control device 76 controls the imaging timings of both the cameras 73A and 73B. The imaging timings are controlled, based on the signals from the encoders of the respective rotating drums 55 and 58 described above. The cameras 73A and 73B take images every time the rotating drums 55 and 58 are rotated by predetermined amounts.

The CPU and input/output interface 77 takes charge of various controls with regard to the appearance inspection device 71. For example, the CPU and input/output interface 77 executes various processing programs and determines the quality of the tablet 5 based on the obtained image data. The CPU and input/output interface 77 also serves to send and receive various signals to and from the control device 81. Additionally, the CPU and input/output interface 77 increments the serial number of the expected sheet portion 7 by one every time the downstream side rotating drum 58 is rotated by a predetermined amount, and identifies the correspondence relationship between the serial number and the tablets 5 that are to be supplied to the expected sheet portion 7 identified by the serial number. This configuration enables the information regarding the quality determination results of the respective tablets 5 indicated by the tablet numbers J1 to J10 to be related to the serial number identifying the expected sheet portion 7, to which these tablets 5 are to be supplied, and to be stored in the inspection result storage device 75B.

According to one or more embodiments of the present invention, the quality determination results of the tablets 5 are derived almost immediately after the image data are obtained by the cameras 73A and 73B, and the information regarding the derived quality determination results are promptly sent to the control device 81. This configuration derives the quality determination results of the respective tablets 5 that are to be supplied to one expected sheet portion 7, before the upstream side sucking portions 55A that suck the respective tablets 5 and are to transfer the respective tablets 5 to the corresponding downstream side sucking portions 58A reach the chute corresponding position P1.

The following describes the control device 81. Like the quality determination device 74 described above, the control device 81 is configured as a computer system. According to one or more embodiments of the present invention, the control device 81 corresponds to the sucking state control unit and the supply control unit.

The control device 81 is electrically connected with the main body device 51 and with the appearance inspection device 71 and is configured to receive information regarding the rotation amounts of the rotating drums 55 and 58 from the main body device 51 and to receive information regarding the quality determination results from the appearance inspection device 71. The control device 81 identifies the positions of the sucking portions 55A and 58A, based on the information of the rotating drums 55 and 58. The control device 81 also identifies the qualities of the respective tablets 5 in each expected sheet portion 7, based on the information from the appearance inspection device 71.

Additionally, the control device 81 controls the main body device 51 based on the quality determination results of the tablets 5, so as not to supply any non-defective tablets 5 to the expected sheet portion 7 to which the tablet 5 determined as a defective as well as the other non-defective tablets 5 are to be supplied.

More specifically, the control device 81 first executes a process of setting a changeover schedule of the electromagnetic changeover valves 65 and a supply schedule of the supply chutes 53, based on the quality determination results of the tablets 5 (operation schedule setting process). The set changeover schedule of the electromagnetic changeover valves 65 is added to and stored in a sucking changeover schedule table KT1 (shown in FIGS. 16 and 18) in the RAM of the control device 81. The set supply schedule of the supply chutes 53 is added to and stored in a supply changeover schedule table KT2 (shown in FIGS. 17 and 19) in the RAM.

Figure 16:
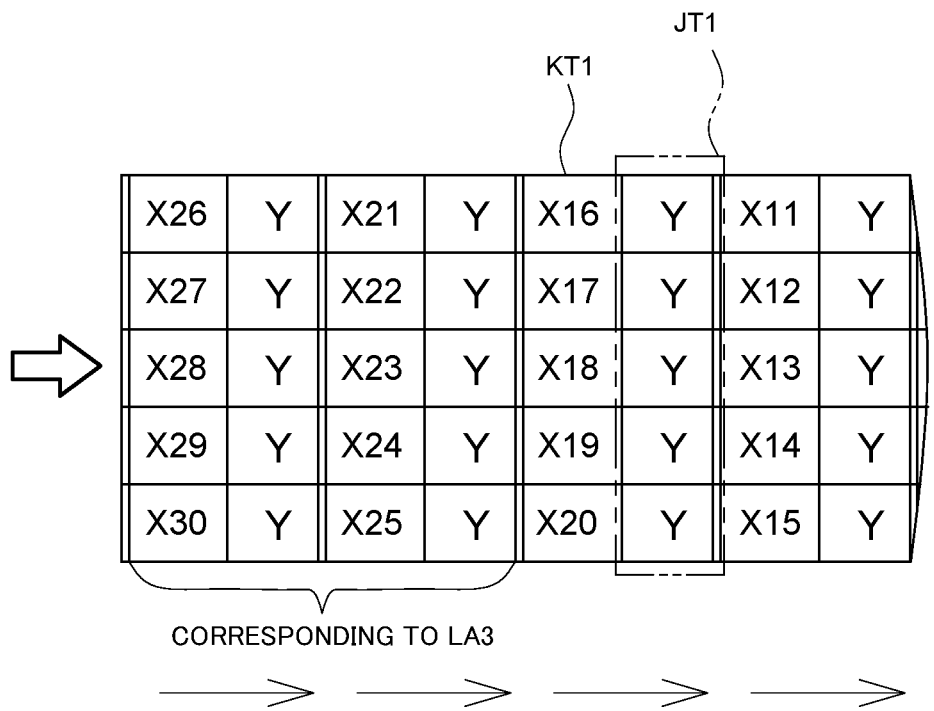
FIG. 16 is a diagram illustrating one example of a sucking changeover schedule table according to one or more embodiments of the present invention.
Figure 17:
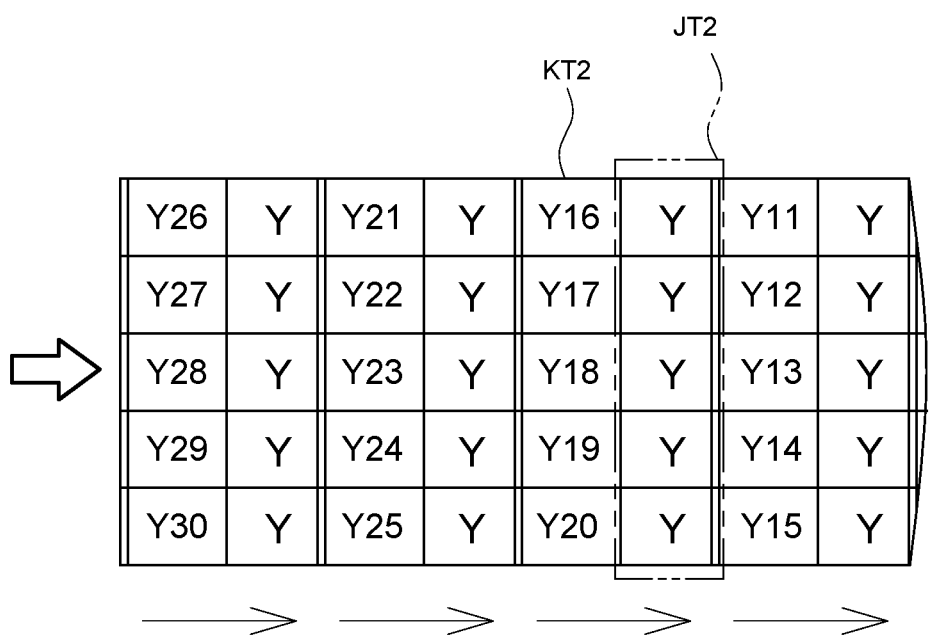
FIG. 17 is a diagram illustrating one example of a supply changeover schedule table according to one or more embodiments of the present invention.
Figure 18:
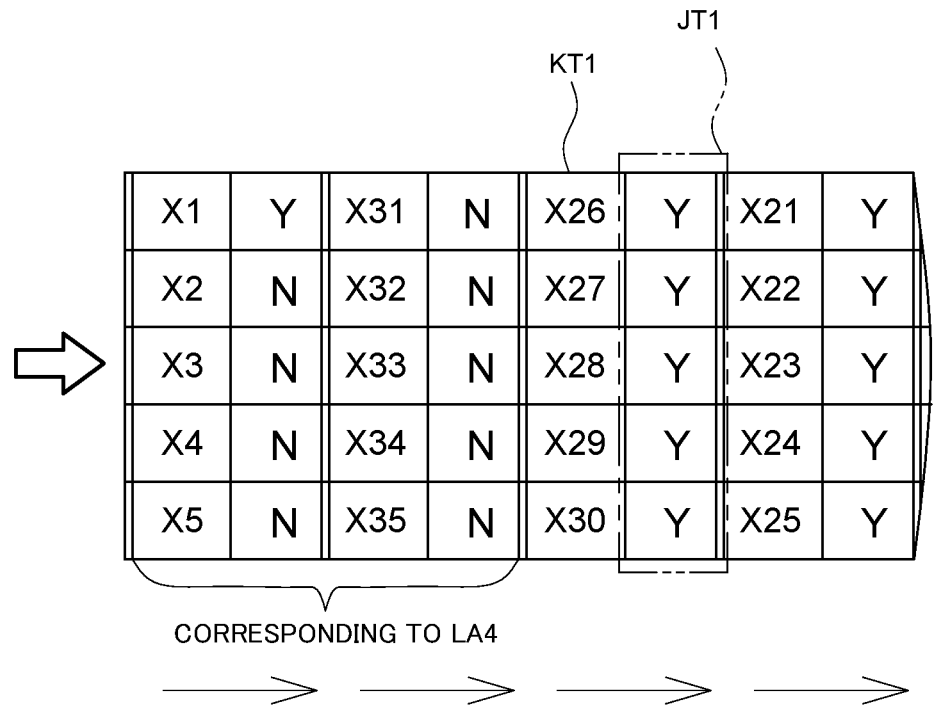
FIG. 18 is a diagram illustrating one example of the sucking changeover schedule table according to one or more embodiments of the present invention.
Figure 19:
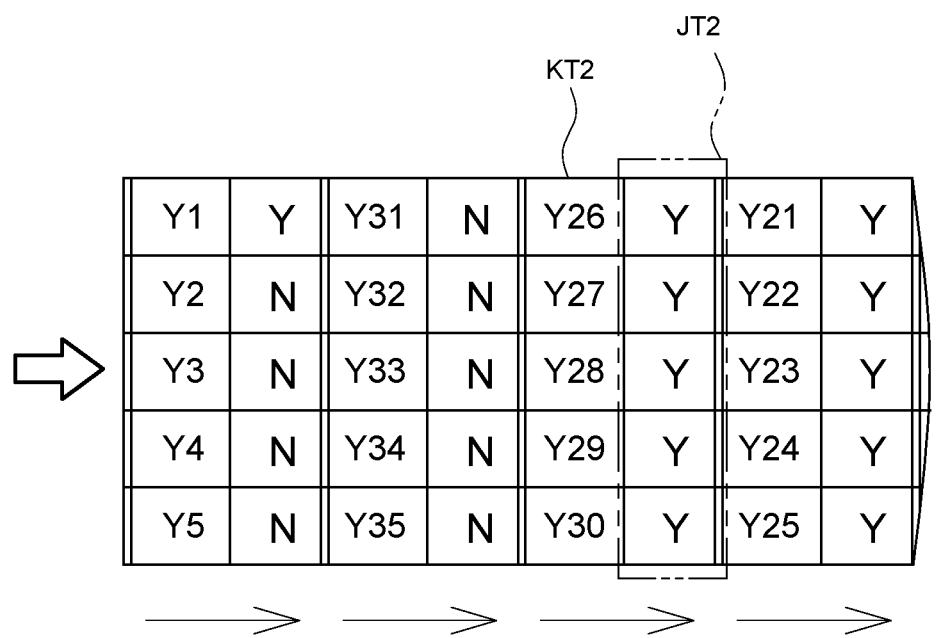
FIG. 19 is a diagram illustrating one example of the supply changeover schedule table according to one or more embodiments of the present invention.

In FIG. 16 and FIG. 18, "Y" indicates that the electromagnetic changeover valve 65 is operated to open the changeover space S4 to the open air, and "N" indicates that the electromagnetic changeover valve 65 is operated to apply negative pressure to the changeover space S4. In FIG. 17 and FIG. 19, "Y" indicates that the supply chute 53 is opened to supply the tablet 5 to the upstream side sucking portion 55A, and "N" indicates that the supply chute 53 is closed not to supply the tablet 5 to the upstream side sucking portion 55A. In order to facilitate explanation, FIGS. 16 to 19 additionally show the reference signs X1 to X35 of the sucking portions 55A and the reference signs Y1 to Y35 of the sucking portions 58A corresponding to the electromagnetic changeover valves 65 as operation objects.

The control device 81 shifts data in the sucking changeover schedule table KT1 at every predetermined timing (for example, every time the downstream side sucking portion 58A reaches the imaging position P3), so as to sequentially shift data regarding the changeover schedule of the electromagnetic changeover valves 65 corresponding to the downstream side sucking portions 58A aligned in the axis direction of the downstream side rotating drum 58 to a predetermined working table JT1 (shown in FIGS. 16 and 18). The control device 81 then controls the operations of the electromagnetic changeover valves 65, based on the data of the working table JT1, at a timing immediately before the respective downstream side sucking portions 58A corresponding to the data in the working table JT1 reach the filling position P4. The control timing of the operations of the electromagnetic changeover valves 65 is determined, based on the signal from the encoder of the downstream side rotating drum 58.

The control device 81 also shifts data in the supply changeover schedule table KT2 at every predetermined timing (for example, every time the upstream side sucking portion 55A reaches the chute corresponding position P1), so as to sequentially shift data regarding the supply schedule of the supply chutes 53 corresponding to the upstream side sucking portions 55A aligned in the axis direction of the upstream side rotating drum 55 to a predetermined working table JT2 (shown in FIGS. 17 and 19). The control device 81 then controls the operations of the supply chutes 53, based on the data of the working table JT2, at a timing immediately before the respective upstream side sucking portions 55A corresponding to the data in the working table JT2 reach the chute corresponding position P1. The control timing of the operations of the supply chutes 53 is determined, based on the signal from the encoder of the upstream side rotating drum 55.

The following describes the process of setting the changeover schedule of the electromagnetic changeover valves 65 and the supply schedule of the supply chutes 53, based on the quality determination results of the tablets 5 (operation schedule setting process).

Figure 20:
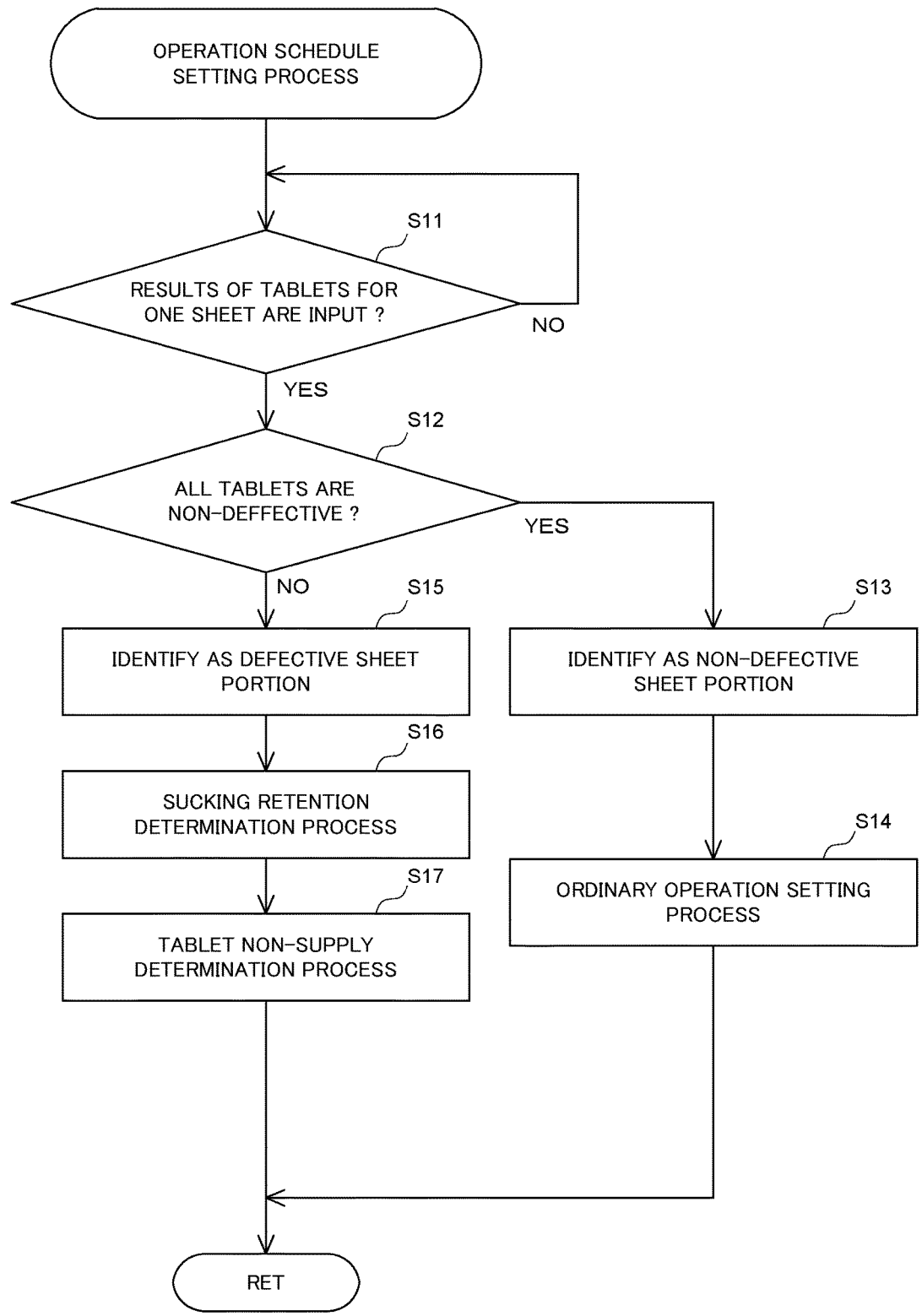
FIG. 20 is a flowchart showing an operation schedule setting process according to one or more embodiments of the present invention.

As shown in FIG. 20, the operation schedule setting process first determines whether information regarding quality determination results of tablets 5 that are to be supplied to one expected sheet portion 7 (tablets 5 for one sheet) is input into the control device 81 at step S11. According to one or more embodiments of the present invention, it is determined whether information regarding quality determination results of ten tablets 5 corresponding to one expected sheet portion 7 is input. The processing of step S11 is repeated until information regarding the quality determination results of the tablets 5 for one sheet is input. When information regarding the quality determination results of the tablets 5 for one sheet is input (step S11: YES), the process proceeds to step S12.

At step S12, the operation schedule setting process determines whether all the tablets 5 for one sheet are non-defective products. When all the tablets 5 are non-defective products (step S12: YES), the process proceeds to step S13.

The operation schedule setting process identifies the expected sheet portion 7 to which the tablets 5 as determination objects are to be supplied, as a non-defective sheet portion at step S13 and then proceeds to step S14. The operation schedule setting process executes an ordinary operation setting process at subsequent step S14 and then returns to step S11.

The ordinary operation setting process sets an operation schedule of the main body device 51 to supply tablets 5 to the non-defective sheet portion and to supply new tablets 5 to the downstream side sucking portions 58A from which the tablets 5 are supplied to the non-defective sheet portion.

More specifically, the ordinary operation setting process sets a changeover schedule of the electromagnetic changeover valves 65 such that the downstream side vacuum ports 58B of the respective downstream side sucking portions 58A corresponding to the non-defective sheet portion are open to the atmosphere at the filling position P4, and adds and stores the set changeover schedule to and in the operation schedule table KT1. For example, when an expected sheet portion 7 indicated by a serial number LA3 is identified as a non-defective sheet portion, the changeover schedule of the corresponding electromagnetic changeover valves 65 is set such that downstream side vacuum ports 58B of downstream side sucking portions 58A indicated by reference signs X21 to X30 corresponding to tablets 5 that are to be supplied to this non-defective sheet portion are opened to the atmosphere (as shown in FIG. 16). The set changeover schedule is added to and stored in the sucking changeover schedule table KT1.

The ordinary operation setting process also sets a supply schedule of the supply chutes 53 such that new tablets 5 are supplied to the respective downstream side sucking portions 58A corresponding to the respective tablets 5 that are to be supplied to the non-defective sheet portion, and adds and stores the set supply schedule to and in the supply changeover schedule table KT2. For example, when the expected sheet portion 7 indicated by the serial number LA3 is identified as a non-defective sheet portion, the supply schedule of the supply chutes 53 is set such that tablets 5 are to be supplied at the supply position P2 to upstream side sucking portions 55A indicated by reference signs Y21 to Y30 corresponding to the downstream side sucking portions 58A indicated by the reference signs X21 to X30 (as shown in FIG. 17). The set supply schedule is added to and stored in the supply changeover schedule table KT2.

When at least one of the tablets 5 for one sheet is a defective (step S12: NO), on the other hand, the operation schedule setting process proceeds to step S15 to identify an expected sheet portion 7 to which the defective tablet 5 is to be supplied, as a defective sheet portion. For example, when at least one of tablets 5 that are to be supplied to an expected sheet portion 7 indicated by a serial number LA4 is determined as a defective, this expected sheet portion 7 is identified as a defective sheet portion.

At step S16 subsequent to step S15, the operation schedule setting process executes a sucking retention determination process. This process sets the changeover schedule of the electromagnetic changeover valves 65 to apply negative pressure to the downstream side vacuum ports 58B corresponding to the tablets 5 determined as non-defective products among the downstream side vacuum ports 58B of the respective downstream side sucking portions 58A corresponding to the defective sheet portion and to cause the downstream side vacuum port 58B corresponding to the tablet 5 determined as a defective to be open to the atmosphere at the filling position P4. The set changeover schedule is then added to and stored in the sucking changeover schedule table KT1. For example, it is assumed that an expected sheet portion 7 indicated by a serial number LA4 is identified as a defective sheet portion (as shown in FIG. 14). In this case, with regard to the downstream side sucking portions 58A indicated by the reference signs X2 to X5 and X31 to X35 corresponding to the tablets 5 determined as non-defective products among the tablets 5 that are to be supplied to this defective sheet portion, the changeover schedule of the electromagnetic changeover valves 65 is set to apply negative pressure to the corresponding downstream side vacuum ports 58B (as shown in FIG. 18). With regard to the downstream side sucking portion 58A indicated by the reference sign X1 corresponding to the tablet 5 determined as a defective, on the other hand, the changeover schedule of the electromagnetic changeover valve 65 is set to cause the corresponding downstream side vacuum port 57B to be open to the atmosphere (as shown in FIG. 18). The set changeover schedule is then added to and stored in the sucking changeover schedule table KT1. Setting and storing the changeover schedule as described above supplies only the tablet 5 determined as a defective to the defective sheet portion, while not supplying the tablets 5 determined as non-defective products to the defective sheet portion.

The operation schedule setting process executes a tablet non-supply determination process at subsequent step S17 and then returns to step S11. The tablet non-supply determination process sets the supply schedule of the supply chutes 53 to supply a new tablet 5 to the downstream side sucking portion 58A corresponding to the defective tablet 5 but not to supply new tablets 5 to the downstream side sucking portions 58A corresponding to the non-defective tablets 5, among the tablets 5 that are to be supplied to the defective sheet portion. The set supply schedule is then added to and stored in the supply changeover schedule table KT2. For example, it is assumed that the expected sheet portion 7 indicated by the serial number LA4 is identified as a defective sheet portion (as shown in FIG. 14). In this case, the supply schedule of the supply chutes 53 is set not to supply the tablets 5 to the upstream side sucking portions 55A indicated by the reference signs Y2 to Y5 and Y31 to Y35 corresponding to the downstream side sucking portions 58A indicated by the reference signs X2 to X5 and X31 to X35 (as shown in FIG. 19). The supply schedule of the supply chute 53 is set, on the other hand, to supply the tablet 5 to the upstream side sucking portion 55A indicated by the reference sign Y1 corresponding to the downstream side sucking portion 58A indicated by the reference sign X1 (as shown in FIG. 19). The set supply schedule is then added to and stored in the supply changeover schedule table KT2. Setting and storing the supply schedule as described above supplies the tablet 5 to only the downstream side sucking portion 58A that does not suck and hold the tablet 5, while not supplying the tablets 5 to the downstream side sucking portions 58A that already such and hold the tablets 5.

As described above in detail, according to one or more embodiments of the present invention, when the quality determination device 74 provides a defective determination, the non-defective tablets 5 are not supplied to the expected sheet portion 7 to which the tablets 5 involved in this defective determination are to be supplied (defective sheet portion) at the filling position P4 but are kept sucked by the downstream side sucking portions 58A. A punched-out defective sheet accordingly does not include any non-defective tablet 5. This configuration does not need to take out the non-defective tablets 5 from the defective sheet with a view to reusing the non-defective tablets 5 and does not waste the non-defective tablets 5 even when the defective sheet is disposed directly.

Additionally, the downstream side sucking portion 58A that sucks and holds a non-defective tablet 5 is moved again to the supply position P2 and to the filling position P4 along with rotation of the downstream side rotating drum 58. No new tablet 5 is, however, supplied to this downstream side sucking portion 58A at the supply position P2, and this downstream side sucking portion 58A is moved to the filling position P4 while maintaining the suction and retention of the non-defective tablet 5. When all the other tablets 5 that are to be supplied to the expected sheet portion 7 to which this non-defective tablet 5 is to be supplied, are non-defective, this non-defective tablet 5 is filled into the pocket portion 2 at the filling position P4. Accordingly, non-defective tablets 5 involved in a defective sheet portion are neither filled into the pocket portions 2 nor recovered from the pocket portions 2 but are kept in the state of suction and retention at the filling position P4 to be used for subsequent filling.

As described above, the configuration according to one or more embodiments of the present invention does not waste but uses the non-defective tablets 5 with no special effort, while more effectively preventing damage of the tablets 5. This configuration does not require any separate device for recovery of the tablets 5 and thereby achieves simplification of the apparatus and reduction of various costs.

Figure 21:
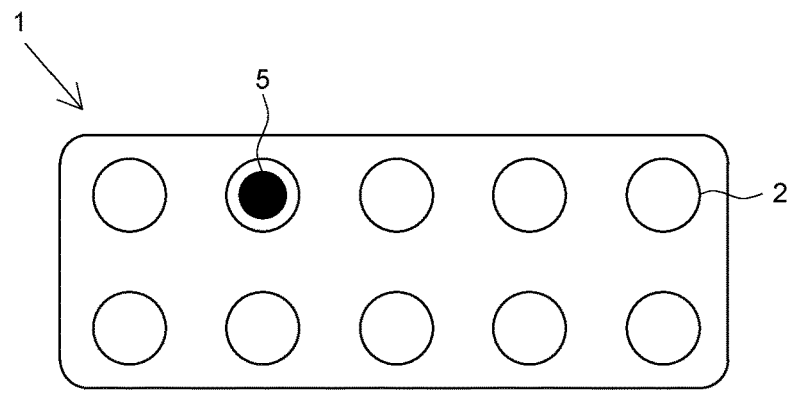
FIG. 21 is a plan diagram illustrating one example of a PTP sheet discharged as a defective according to one or more embodiments of the present invention.

Furthermore, the configuration according to one or more embodiments of the present invention supplies only the defective tablet 5 to the defective sheet portion, while not supplying the non-defective tablets 5. Accordingly, only a defective tablet 5 is filled in the pocket portion 2 in an eventually obtained PTP sheet 1 corresponding to the defective sheet portion as shown in FIG. 21. This configuration enables the type of abnormality to be readily identified by observation of the filled tablet 5. As a result, this configuration readily identifies the inspection item of the abnormality and enables appropriate measures to be taken promptly.

The defective tablet 5 is supplied to the defective sheet portion. This configuration does not require any device for separately discharging defective tablets 5. This more effectively achieves simplification of the apparatus and reduction of various costs.

Additionally, one or more embodiments of the present invention are configured to use the two rotating drums 55 and 58 to reverse the sucked face of the tablet 5 by the sucking portions 55A and 58A. This configuration enables the image of the side face 5A, the surface 5B and the rear face 5C of the tablet 5 to be taken by the cameras 73A and 73B. This configuration accordingly allows for the quality determination with regard to the entire outer surface of the tablet 5 and thereby ensures the more accurate quality determination.

The quality determination is executed, based on image data including data regarding the side face 5A. There is accordingly no need to execute the quality determination of the side face 5A separately from that of the surface 5B and the rear face 5C. As a result, this configuration shortens the time period required for the quality determination and increases the efficiency of inspection.

Furthermore, one or more embodiments of the present invention are configured to change over between the supply and non-supply of the tablet 5 from the supply chute 53 to the upstream side sucking portion 55A, so as to change over between supply and non-supply of the tablet 5 to the downstream side sucking portion 58A located at the supply position P2. This configuration uses the two rotating drums 55 and 58 to enhance the accuracy of the quality determination, while readily changing over between supply and non-supply of the tablet 5 to the downstream side sucking portion 58A.

Additionally, the time period required from the time when all the downstream side sucking portions 58A corresponding to one expected sheet portion 7 reach the imaging position P3 to the time when at least one of these downstream side sucking portions 58A reaches the supply position P2 is longer than the time period required when the upstream side sucking portion 55A is moved from the chute corresponding position P1 to reach the supply position P2. This configuration enables the retention or the cancellation of the sucking state of a tablet 5 sucked by a predetermined downstream side sucking portion 58A to be determined more reliably before a predetermined upstream side sucking portion 55A that is to transfer the tablet 5 to the predetermined downstream side sucking portion 58A reaches the chute corresponding position P1. This configuration accordingly enables supply or non-supply of the tablet 5 to the predetermined upstream side sucking portion 55A to be determined more reliably before the predetermined upstream side sucking portion 55A reaches the chute corresponding position P1.

The disclosure is not limited to the descriptions of the above embodiments but may be implemented, for example, as described below. There are naturally other applications and modifications, in addition to those described below.

Figure 22:
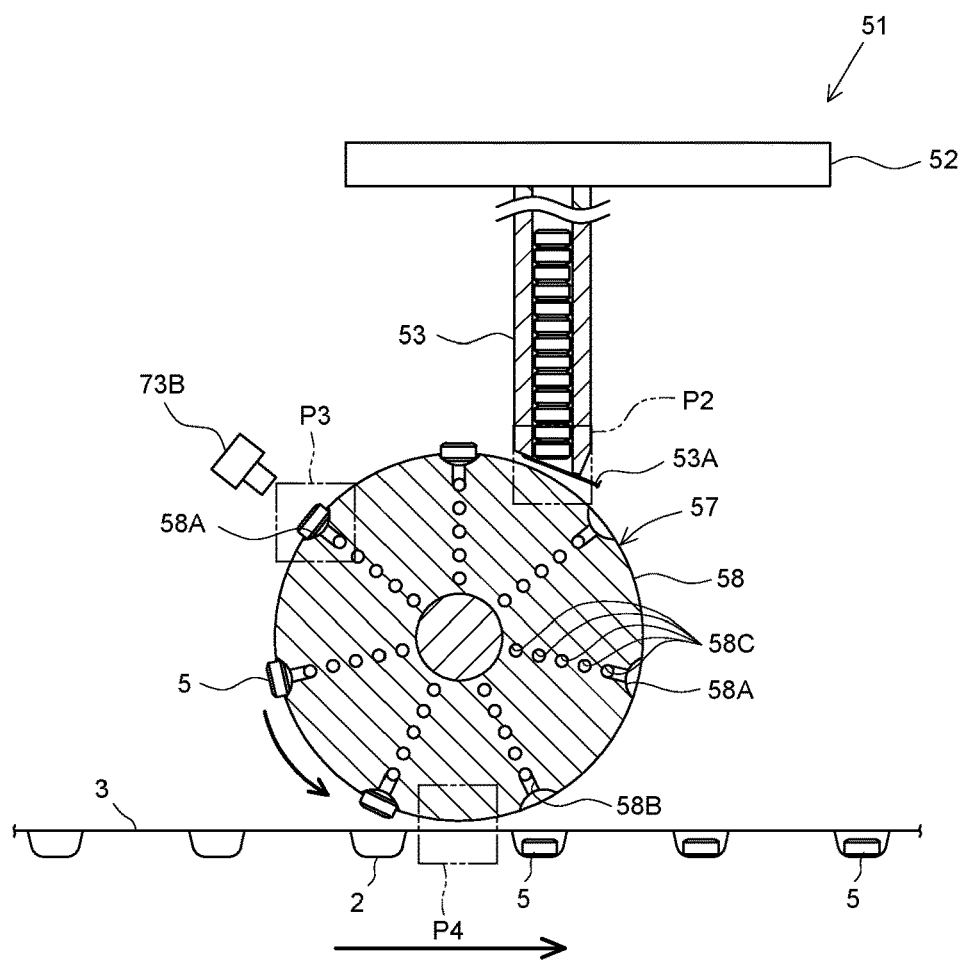
FIG. 22 is a diagram illustrating the schematic configuration of another main body device according to one or more embodiments of the present invention.

(a) In the main body device 51 according to the above embodiments, the supply unit is configured by the upstream side drum 54 and the supply chutes 53. According to a modification, the supply unit may be configured by only the supply chutes 53 as shown in FIG. 22. This modification is configured to supply the tablets 5 directly to the downstream side rotating drum 58 without going through the upstream side drum 54.

Figure 23:
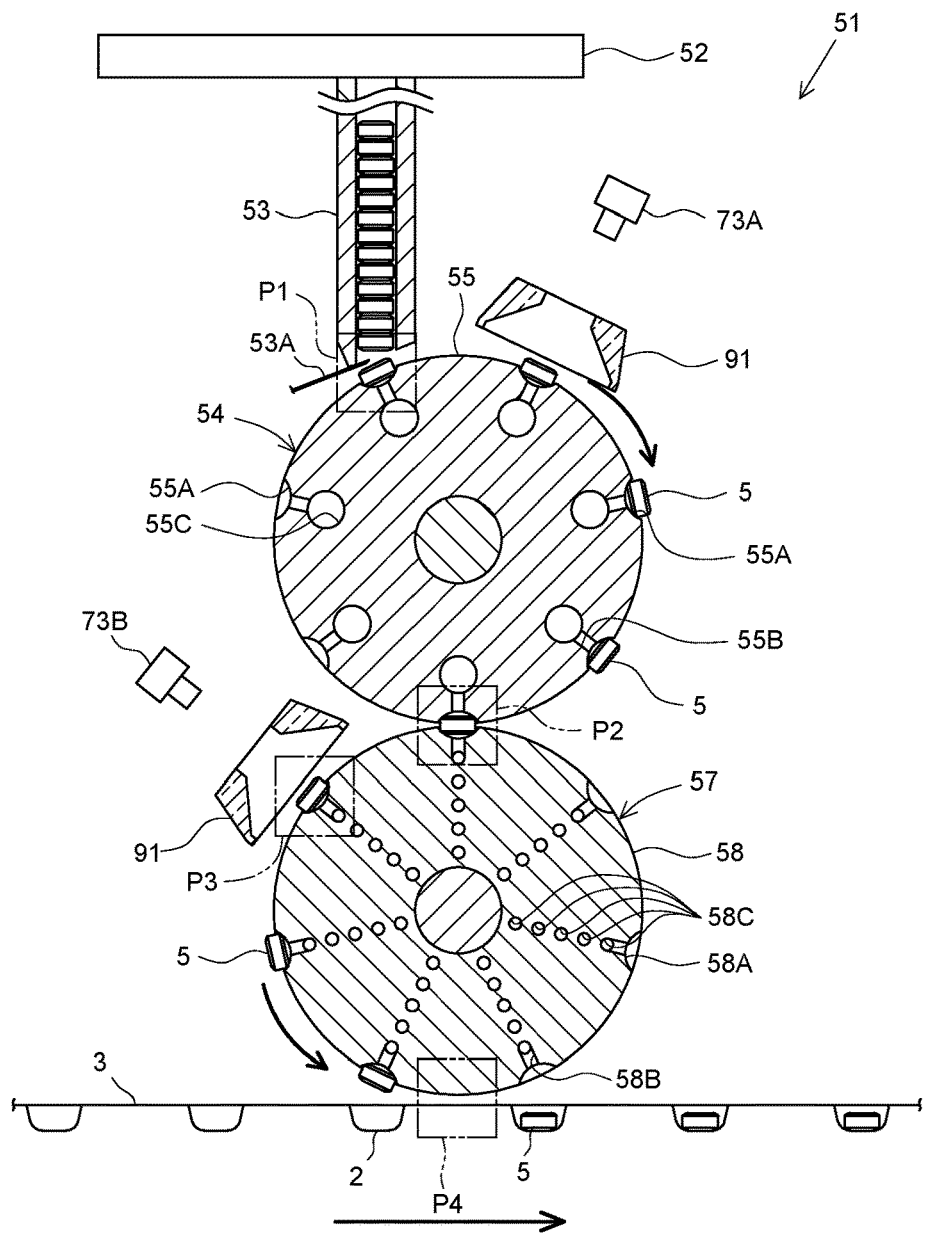
FIG. 23 is a diagram illustrating the schematic configuration of another main body device according to one or more embodiments of the present invention.
Figure 24:
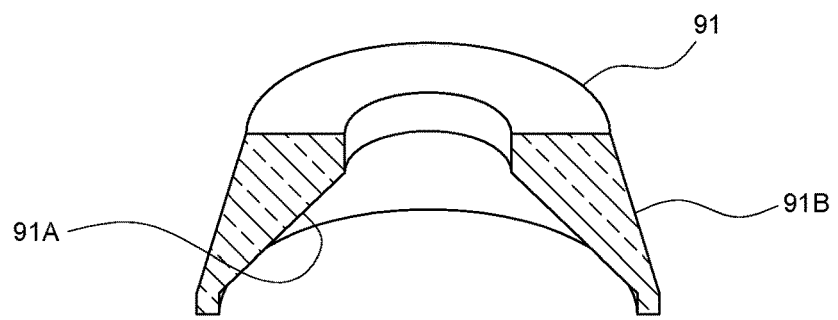
FIG. 24 is a sectional perspective view illustrating the schematic configuration of a prism according to one or more embodiments of the present invention.

(b) The above embodiments are configured to use the convex lens and adjust the focal length, in order to take an image of the side face 5A of the tablet 5 by the cameras 73A and 73B. According to a modification, prisms 91 may be used to take an image of the side face 5A as shown in FIG. 23 and FIG. 24. The prism 91 includes, for example, an inner circumferential face 91A and an outer circumferential face 91B that are respectively formed in truncated cone shapes and is placed between the camera 73A or 73B and the tablet 5 as an imaging object. The light transmitted through the inner circumferential face 91A and reflected by the side face 5A is reflected by the outer circumferential face 91B and is subsequently reflected by the inner circumferential face 91A to enter the camera 73A or 73B, so that an image of the side face 5A is taken. This modification more effectively suppresses distortion of the side face 5A in the obtained image data and further improves the accuracy of the quality determination, compared with the above embodiments.

(c) The above embodiments are configured to supply the tablet 5 determined as a defective to the defective sheet portion. According to a modification, the tablet 5 determined as a defective may be discharged to a predetermined defective discharge portion (for example, a container to accumulate defective tablets 5 therein). In the case where the tablet 5 is removed from the downstream side sucking portion 58A for such discharge, for example, the tablet 5 may be removed by bringing a predetermined claw-like member into contact with the tablet 5 or may be removed by supplying the air to the downstream side vacuum port 58B.

(d) The above embodiments concretely describe the configuration for the tablet 5 as the content. The type, the shape and the like of the content are, however, not specifically limited. The content may be different from the tablet 5, for example, a capsule, an electronic component or a food item.

(e) According to the above embodiments, the container film 3 is formed from the transparent or translucent thermoplastic resin material such as PP or PV, and the cover film 4 is formed by using aluminum foil or the like as the base material. The materials of the respective films 3 and 4 are, however, not limited to these materials but may be other materials.

(f) The configuration of the appearance inspection device 71 is not limited to that of the above embodiments. The inspection items described in the above embodiments are only illustrative and may be changed appropriately.

(g) The above embodiments are configured to execute the quality determination with regard to the tablets 5 sucked by the sucking portions 55A and 58A after being supplied to the rotating drums 55 and 58. A modification may be configured to execute the quality determination with regard to the tablets 5 before being supplied to the rotating drums 55 and 58.

(h) The arrangement and the number of the pocket portions 2 in the PTP sheet 1 are not limited to those (two arrays, ten pocket portions) described in the above embodiments. A PTP sheet having any of various arrangements and any of various numbers of pocket portions may be employed; for example, a PTP sheet having twelve pocket portions arranged in three arrays.

(i) According to the above embodiments, the PTP film 6 is configured such that the number of pocket portions 2 corresponding to one sheet are arrayed along its width direction. This configuration is, however, not essential. For example, the PTP film may be configured such that the number of pocket portions 2 corresponding to multiple sheets are arrayed along its width direction. The configuration of the filling device 21 may be modified appropriately, for example, according to the arrangement of the pocket portions 2 in the PTP film 6.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims

REFERENCE SIGNS LIST

1 . . . PTP sheet, 2 . . . pocket portion, 3 . . . container film, 4 . . . cover film, 5 . . . tablet (content), 6 . . . PTP film, 11 . . . PTP packaging machine, 20 . . . film receiving roll (sealing unit), 21 . . . filling device (filling unit), 26 . . .

heating roll (sealing unit), 37 . . . sheet punching device (punching unit), 53 . . . supply chute, 53A . . . shutter (supply changeover unit), 55 . . . upstream side rotating drum, 55A . . . upstream side sucking portion, 58 . . . downstream side rotating drum (rotating drum), 58A . . . downstream side sucking portion (sucking portion), 65 . . . electromagnetic changeover valve (sucking state changeover unit), 73A . . . upstream side camera (second imaging unit), 73B . . . downstream side camera (first imaging unit), 74 . . . quality determination device (quality determination unit), 81 . . . control device (sucking state control unit, supply control unit), P1 . . . chute corresponding position, P2 . . . supply position, P3 . . . imaging position, P4 . . . filling position

What is claimed is:

1. A PTP packaging machine, comprising:
   a filler that fills a predetermined content into pocket portions formed in a strip-shaped container film;
   a sealer that is provided on a downstream side of the filler and mounts a strip-shaped cover film to the container film to close the pocket portions and obtain a strip-shaped PTP film including the cover film mounted to the container film; and
   a puncher that is provided on a downstream side of the sealer and punches out an expected sheet portion of the PTP film that is a region of eventually forming a predetermined PTP sheet and thereby obtain the PTP sheet, wherein
   the filler comprises:
      a first rotating drum having a plurality of first sucking portions that are formed in an outer circumference of the first rotating drum and suck the content, wherein each of the first sucking portions moves from a predetermined supply position through a predetermined filling position and returns to the supply position, along with rotation of the first rotating drum;
      a supplier comprising:
         a supply chute that has an opening and supplies the content through the opening; and
         a shutter that changes over between a first state and a second state, wherein the shutter in the first state opens the opening and allows the supply chute to supply the content to each of the first sucking portions located at the supply position, and the shutter in the second state closes the opening and prevents the supply chute from supplying the content;
      a changeover valve that individually changes over each of the first sucking portions to a sucking state or a non-sucking state, and sets each of the first sucking portions in the non-sucking state at the filling position to fill the content from each of the first sucking portions into each of the pocket portions or keeps each of the first sucking portions in the sucking state at the filling position not to fill the content into each of the pocket portions;
      an imager that takes an image of the content sucked or to be sucked by each of the first sucking portions at a stage before each of the first sucking portions reaches the filling position;
      a first controller that determines quality of appearance of the content, based on image data obtained by the imager; and
      a second controller that controls the changeover valve based on a determination result by the first controller, and that controls the shutter based on the determination result by the first controller, wherein
      upon identifying, as a defective sheet portion, the expected sheet portion including, among the pocket portions, a pocket portion in which the content determined as a defective by the first controller is to be filled,
      the second controller:
         controls the changeover valve to maintain each of the first sucking portions holding the content determined as a non-defective product by the first controller, among the contents to be filled into the pocket portions of the defective sheet portion, in the sucking state at least at the filling position, and
         controls the shutter to close the opening to prevent the supply chute from supplying the content to each of the first sucking portions holding the content determined as the non-defective product when the each of the first sucking portions holding the content determined as the non-defective product returns to the supply position.

2. The PTP packaging machine according to claim 1, wherein
   the second controller controls the changeover valve to set each of the first sucking portions holding the content determined as the defective by the first controller, among the contents to be filled into the pocket portions of the defective sheet portion, in the non-sucking state at least at the filling position.

3. The PTP packaging machine according to claim 2, wherein
   the supplier comprises a second rotating drum having a plurality of second sucking portions that are formed in an outer circumference of the second rotating drum and suck the content, the second rotating drum transferring the content sucked by each of the second sucking portions, to each of the first sucking portions at the supply position, and
   the imager comprises:
      a first imager that takes an image of at least an opposite face that is opposite to a sucked face of the content sucked by each of the first sucking portions; and
      a second imager that takes an image of at least an opposite face that is opposite to a sucked face of the content sucked by each of the second sucking portions, wherein
      the sucked face of the content is reversed in a process of transferring the content from each of the second sucking portions to each of the first sucking portions.

4. The PTP packaging machine according to claim 3, wherein
   the shutter in the first state opens the opening and allows the supply chute to supply the content to each of the second sucking portions so as to supply the content to each of the first sucking portions located at the supply position,
   the first imager takes an image of the content when each of the first sucking portions reaches a predetermined imaging position, and
   a time period required from a time when all the first sucking portions corresponding to each of the expected sheet portion reach the imaging position to a time when at least one of the first sucking portions corresponding to each of the expected sheet portion reaches the supply position is set to be longer than a time period required when each of the second sucking portions moves from the supply chute corresponding position to reach the supply position.

5. The PTP packaging machine according to claim 4, wherein
the first imager and the second imager take an image of a side face of the content, wherein the side face is located between the sucked face by each of the first sucking portions and the sucked face by each of the second sucking portions.

6. The PTP packaging machine according to claim 3, wherein
the first imager and the second imager take an image of a side face of the content, wherein the side face is located between the sucked face by each of the first sucking portions and the sucked face by each of the second sucking portions.

7. The PTP packaging machine according to claim 1, wherein
the supplier comprises a second rotating drum having a plurality of second sucking portions that are formed in an outer circumference of the second rotating drum to suck the content, the second rotating drum transferring the content sucked by the second sucking portions, to the first sucking portions at the supply position, and
the imager comprises:
a first imager that takes an image of at least an opposite face that is opposite to a sucked face of the content sucked by the first sucking portions; and
a second imager that takes an image of at least an opposite face that is opposite to a sucked face of the content sucked by the second sucking portions, wherein
the sucked face of the content is reversed in a process of transferring the content from the second sucking portions to the first sucking portions.

8. The PTP packaging machine according to claim 7, wherein
the shutter in the first state opens the opening and allows the supply chute to supply the content to each of the second sucking portions so as to supply the content to each of the first sucking portions located at the supply position,
the first imager takes an image of the content when each of the first sucking portions reaches a predetermined imaging position, and
a time period required from a time when all the first sucking portions corresponding to each of the expected sheet portion reach the imaging position to a time when at least one of the first sucking portions corresponding to each of the expected sheet portion reaches the supply position is set to be longer than a time period required when each of the second sucking portions moves from the supply chute corresponding position to reach the supply position.

9. The PTP packaging machine according to claim 8, wherein
the first imager and the second imager take an image of a side face of the content, wherein the side face is located between the sucked face by each of the first sucking portions and the sucked face by each of the second sucking portions.

10. The PTP packaging machine according to claim 7, wherein
the first imager and the second imager take an image of a side face of the content, wherein the side face is located between the sucked face by each of the first sucking portions and the sucked face by each of the second sucking portions.

* * * * *